(12) United States Patent
Sabin et al.

(10) Patent No.: US 9,166,347 B2
(45) Date of Patent: Oct. 20, 2015

(54) PERCUTANEOUS POWER DELIVERY SYSTEM FOR PERMANENTLY IMPLANTED MEDICAL DEVICES AND MANUFACTURING METHOD

(75) Inventors: Pierre Sabin, Rouen (FR); Pierre-Yves Quelenn, Mont Saint Aignan (FR)

(73) Assignee: PLUGMED HEART (FR)

( * ) Notice: Subject to any disclaimer, the term of this patent is extended or adjusted under 35 U.S.C. 154(b) by 0 days.

(21) Appl. No.: 13/981,817

(22) PCT Filed: Jan. 27, 2012

(86) PCT No.: PCT/EP2012/051373
§ 371 (c)(1),
(2), (4) Date: Jul. 25, 2013

(87) PCT Pub. No.: WO2012/101267
PCT Pub. Date: Aug. 2, 2012

(65) Prior Publication Data
US 2013/0303020 A1 Nov. 14, 2013

Related U.S. Application Data

(60) Provisional application No. 61/467,497, filed on Mar. 25, 2011, provisional application No. 61/566,016, filed on Dec. 2, 2011.

(30) Foreign Application Priority Data

Jan. 27, 2011 (FR) ...................................... 11 50638

(51) Int. Cl.
*H01R 13/73* (2006.01)
*H01R 43/26* (2006.01)
(Continued)

(52) U.S. Cl.
CPC ............... *H01R 13/73* (2013.01); *A61M 39/02* (2013.01); *B22F 3/105* (2013.01); *H01R 43/26* (2013.01);
(Continued)

(58) Field of Classification Search
None
See application file for complete search history.

(56) References Cited

U.S. PATENT DOCUMENTS
5,507,303 A 4/1996 Kuzma
5,562,670 A 10/1996 Braanemark
(Continued)

FOREIGN PATENT DOCUMENTS
EP 2241343 A1 10/2010
FR 2853249 A1 10/2004
(Continued)

OTHER PUBLICATIONS
International Search Report for Application No. PCT/EP2012/051373 dated Jul. 12, 2012.
(Continued)

*Primary Examiner* — Brian T Gedeon
(74) *Attorney, Agent, or Firm* — Lerner, David, Littenberg, Krumholz & Mentlik, LLP

(57) ABSTRACT

The invention relates to a permanent percutaneous electric connection device intended to be fixed in an osseous structure of a patient to electrically connect an internal entity (150) located inside the body of the patient to an entity external to said body. The device encloses electric connection means running from a first connector to be connected to the external entity to a second connector to be connected to the internal entity. The device has an extension member (120) extending from a socket of the first connector. The extension member is designed for full osseous burial into the osseous structure with its free end (121) being substantially flush with the surface of said osseous structure. The device also comprises an electric connection member (130) comprising the second connector securely fastened to the free end of the extension member (120).

32 Claims, 14 Drawing Sheets

(51) Int. Cl.
 A61M 39/02 (2006.01)
 B22F 3/105 (2006.01)
 *A61N 1/375* (2006.01)
 *A61N 1/05* (2006.01)
 *A61B 19/00* (2006.01)

(52) U.S. Cl.
 CPC ......... *A61B 2019/208* (2013.01); *A61N 1/0539* (2013.01); *A61N 1/375* (2013.01); *Y10T 29/49204* (2015.01)

(56) References Cited

U.S. PATENT DOCUMENTS

| | | | |
|---|---|---|---|
| 5,645,740 A | 7/1997 | Naiman et al. | |
| 5,873,368 A * | 2/1999 | Sabin | 128/899 |
| 5,904,646 A | 5/1999 | Jarvik | |
| 6,053,920 A | 4/2000 | Carlsson et al. | |
| 6,840,919 B1 | 1/2005 | Haakansson | |
| 8,454,701 B2 | 6/2013 | Devauchelle et al. | |
| 2004/0176817 A1 | 9/2004 | Wahlstrand et al. | |
| 2010/0048983 A1 | 2/2010 | Ball et al. | |
| 2013/0096602 A1 * | 4/2013 | Kumar | 606/191 |

FOREIGN PATENT DOCUMENTS

| | | |
|---|---|---|
| FR | 2939304 A1 | 6/2010 |
| WO | 9622727 A1 | 8/1996 |
| WO | 9749438 A1 | 12/1997 |
| WO | 0139830 A2 | 6/2001 |
| WO | 2004052455 A1 | 6/2004 |
| WO | 2009018172 A2 | 2/2009 |

OTHER PUBLICATIONS

U.S. Appl. No. 13/905,855, filed on May 30, 2013.

* cited by examiner

PERCUTANEOUS POWER DELIVERY SYSTEM FOR PERMANENTLY IMPLANTED MEDICAL DEVICES AND MANUFACTURING METHOD

CROSS-REFERENCE TO RELATED APPLICATIONS

The present application is a national phase entry under 35 U.S.C. §371 of International Application No. PCT/EP2012/051373, filed Jan. 27, 2012, published in English, which claims priority from French Application No. 1150638, filed Jan. 27, 2011, U.S. Provisional Application No. 61/467,497 filed Mar. 25, 2011, and U.S. Provisional Application No. 61/566,016, filed Dec. 2, 2011, the disclosures of which are hereby incorporated herein by reference.

FIELD OF THE INVENTION

The present invention relates to the implantation of medical devices in the body of an animal, in particular in the human body, especially the implantation of electric connection devices, more particularly to set up an electric connection between an external electric supply and medical apparatus implanted in the body or between a source of bioelectricity to an external medical device.

TECHNICAL BACKGROUND

The substantial development made in electrical equipment designed to be installed inside the body of a patient to rectify failure of a natural organ already implies a capability for transmitting electric power required by this equipment, from a source of external power to the interior of the body if that quantity of energy is too important to be delivered by implanted batteries.

Contactless power-supply techniques using power transmission via transformer already exist. For instance, WO 2004/052455 discloses a device for transcutaneous energy transmission, i.e. a contactless transmission of energy without traversing the skin. Such device is designed to be fixed onto the osseous surface and is not adapted for intra-osseous burial.

Power-supply techniques via percutaneous cranial implants are also known. Electric connectors can be inserted in the abutments to which cables or electric linking ribbons leading to electric power consumer equipment are connected.

U.S. Pat. No. 5,904,646 discloses in particular a percutaneous socket enabling an electric connection between an apparatus implanted in the body of a patient, and an external apparatus such as a power supply. This percutaneous socket is fixed onto the surface of an osseous wall by means of osteosynthesis screws, with all the pieces making up the socket and the cables being therefore submuscular or subcutaneous. However, such an arrangement of the socket is not very reliable and vulnerable to infections propagated from percutaneous passage.

Patent FR 03-04063 also discloses a permanent percutaneous electric connection device, provided to electrically connect an internal entity to a human or animal body with an entity external to said body, this device comprising a plate support provided to be impacted in a bone of said body, and percutaneous means of electric connection which comprise (i) fixed means of electric connection integrated into the plate support, and (ii) removable means of electric connection provided to be coupled electrically to said fixed means of electric connection and connected respectively to supple electric linking means.

Entity located inside the body or internal entity here means any electric consumer apparatus or producer of electric power, arranged or not to receive a command or control signal, and/or any equipment for measuring or sensing provided for generating electric signals.

Entity external to the body or external entity means any equipment near or distant from the body, provided to supply electric power and/or command or control signals, or to receive signals generated by any sensor or electric apparatus inside the body and/or electric power generated by equipment inside the body.

Such a permanent osseointegrated percutaneous electric connection device has a high level of security and reliability which makes it eligible for demanding uses, especially in cardiology and neurology.

In particular, such permanent percutaneous electric connection devices allow a soft tissue reduction around the percutaneous abutment, which reduces risks of infection, especially at the level of the percutaneous passage. However, even though the risk of infection at the level of the percutaneous passage is reduced, it still exists, and the devices of the prior art are not adapted to limit or even stop the propagation of infectious agents. In particular, known permanent percutaneous electric connection devices have no means provided for limiting or preventing any risk of propagation of infectious agents along the electric cable or electric cables connecting the percutaneous socket to the internal apparatus.

An aim of the present invention is therefore to propose a permanent percutaneous electric connection that can be osseointegrated, adapted to soft tissue reduction and can be easily connected and disconnected to a cervical cable.

More precisely, an aim of the present invention is to propose a permanent percutaneous electric connection device designed to be osseointegrated in an osseous structure of a patient, ensuring increased reliability, and reducing the propagation of possible infectious agents.

To make the osseointegration possible, the device must be solidly implanted with precision in a complementary cavity, preferably made in an osseous wall, for example in the thickness of the cranium at a distance from the dura mater, in order to realize what is referred to the "primary stabilization", without which the osseointegration process cannot start. That device setting up must respect certain established surgical principles, indispensable to osseointegration: preparation of the osseous cavity as least traumatic as possible, abundant irrigation with saline serum with minimal heating of the bone, adequate primary stabilisation of the implanted device.

SUMMARY OF THE INVENTION

To this end, there is proposed a permanent percutaneous electric connection device intended to be fixed in an osseous structure of a patient to electrically connect an internal entity located inside the body of the patient to an entity external to said body, characterized in that:
  the device encloses electric connection means running from a first connector to be connected to the external entity to a second connector to be connected to the internal entity, and
  the device comprises:
    a percutaneous socket having a first end comprising the first connector to be connected to the external entity and a second end opposite to the first end, an extension member extending from the second end of the socket forming an angle relative to the socket and being designed to shift the second connector away from the socket by a non-zero distance, wherein the extension member is further designed for full osseous burial into the osseous structure with its free end being substantially flush with the surface of said osseous structure, and an electric connection member securely fastened to the free end of the extension member, said electric connection member comprising the second connector.

Preferable but not limited aspects of such device, taken alone or in combination, are the following:

the percutaneous socket comprises a percutaneous abutment arranged on an anchoring base, wherein:
  the percutaneous abutment comprises the first connector to the external entity,
  the extension member extends from the anchoring base, said anchoring base being designed for full osseous burial in the osseous structure so that the percutaneous abutment protrudes relative to the surface of the osseous structure.

the anchoring base and the percutaneous abutment are monobloc.

the anchoring base and the percutaneous abutment are removable from each other.

the anchoring base of the socket and the extension member are monobloc.

the extension member and the electric connection member are monobloc.

the second end of the socket and the free end of the extension member are separated by a non-zero distance of at least 5 mm, preferably less than 20 mm, and preferably equal to 10 mm.

the extension member comprises a longitudinal portion extending from the socket and a cup-shaped portion forming the free end of said extension member.

the cup-shaped portion is based on a geometry chosen among circular, regular polygonal, irregular polygonal, or a combination thereof.

the electric connection member comprises an extra-osseous lid to be securely fastened onto the free end of the extension member, wherein the second connector is arranged within said extra-osseous lid.

the electric connection member comprises:
  an extra-osseous electric connection element comprising the second connector, and
  a flexible intermediate element for bringing the connection means from the extension member to the extra-osseous electric connection element, wherein the flexible intermediate element is securely fastened to the free end of the extension member on the one hand and to the extra-osseous electric connection element on the other hand.

the flexible intermediate element is overmold onto the free end of the extension member and/or onto the extra-osseous electric connection element.

the flexible intermediate element comprises a mechanical relief system for preventing elongation of the connection means along their longitudinal axis.

the mechanical relief system comprises a textile structure or a biocompatible metallic structure such as a titanium structure.

the socket and the electric connection member have mean planes forming together an angle α of between 0.5° and 40°, preferably of between 1° and 30°, and most preferably of 15°.

the socket and the electric connection member have mean planes parallel to each other.

the socket and/or the extension member have walls in which are made cavities to form honeycomb walls in order to enlarge the surface of contact between the device and an osseous structure into which the device is to be fixed.

the device comprises one or several anchoring means, said anchoring means being part of the base of the socket, and/or of the extension member, in order to anchor the socket and/or the extension member respectively in a cavity (L) made in the osseous structure.

the anchoring means of the socket and/or of the extension member comprise an intra-osseous anchoring system including:
  an anchoring base designed to be inserted in the cavity (L) according to a direction of insertion perpendicular to the bottom of said cavity (L), and
  at least one anchoring element arranged so as to be able to protrude relative to the anchoring base parallel to the bottom of the cavity (L) to mesh with a lateral wall of said cavity (L).

the base of the socket and the extension member both comprise projecting portions protruding from their surface.

said projecting portions are designed to penetrate the lateral wall of the cavity (L) in a depth between 20 micrometers and 2000 micrometers, and preferably in a depth of 400 micrometers.

the projecting portions have a geometric shape to provide a retention effect, said shape being preferably a symmetric shape chosen among a cone shape, a pyramid shape, and/or a polyhedron shape.

the anchoring means comprise a removable anchoring member to be positioned onto the extension member, wherein said removable anchoring member comprises a main body and at least two plates extending from the main body in order to form a shouldering so as to be flush with the surface of the osseous structure at the periphery of the cavity, each plate having at least one through orifice intended to receive an osteosynthesis screw for anchoring in the osseous structure.

the connectors comprise contactless connection means, adapted for transfer of energy or any electrical signal.

the second connector is designed for detachable connection of a cable intended to be connected to the internal entity.

the device further comprises an intermediate connection assembly, intended to be arranged between the electric connection member and the internal entity and adapted to be fixed in the body of the patient.

the device further comprises an electric cable connected detachably to the electric connection member on the one hand and to the intermediate connection assembly on the other hand.

the intermediate connection assembly further comprises an auxiliary socket adapted to be connected to an external power supply, the intermediate connector and the auxiliary socket being electrically connected by an intermediate connecting element.

There is also proposed a manufacturing method of such device, characterised in that it comprises a step during which the socket and the extension member are made by a substractive manufacturing technology.

Alternatively, the manufacturing method of such device is characterised in that it comprises a step during which the socket and the extension member are made by a metals additive manufacturing technology.

BRIEF DESCRIPTION OF THE DRAWINGS

Other advantages and characteristics of the invention will emerge from the detailed description of non-limiting embodiments, and from the attached drawings, wherein.

DETAILED DESCRIPTION OF THE INVENTION

The percutaneous device is provided to electrically connect an internal entity 150 located inside the body of a patient to an entity external to said body. For example, such a percutaneous device can be used to electrically connect external batteries to an implanted apparatus such as VAD ("Ventricular Assist Device"), or a TAH ("Total Artificial Heart").

Figure 1A:
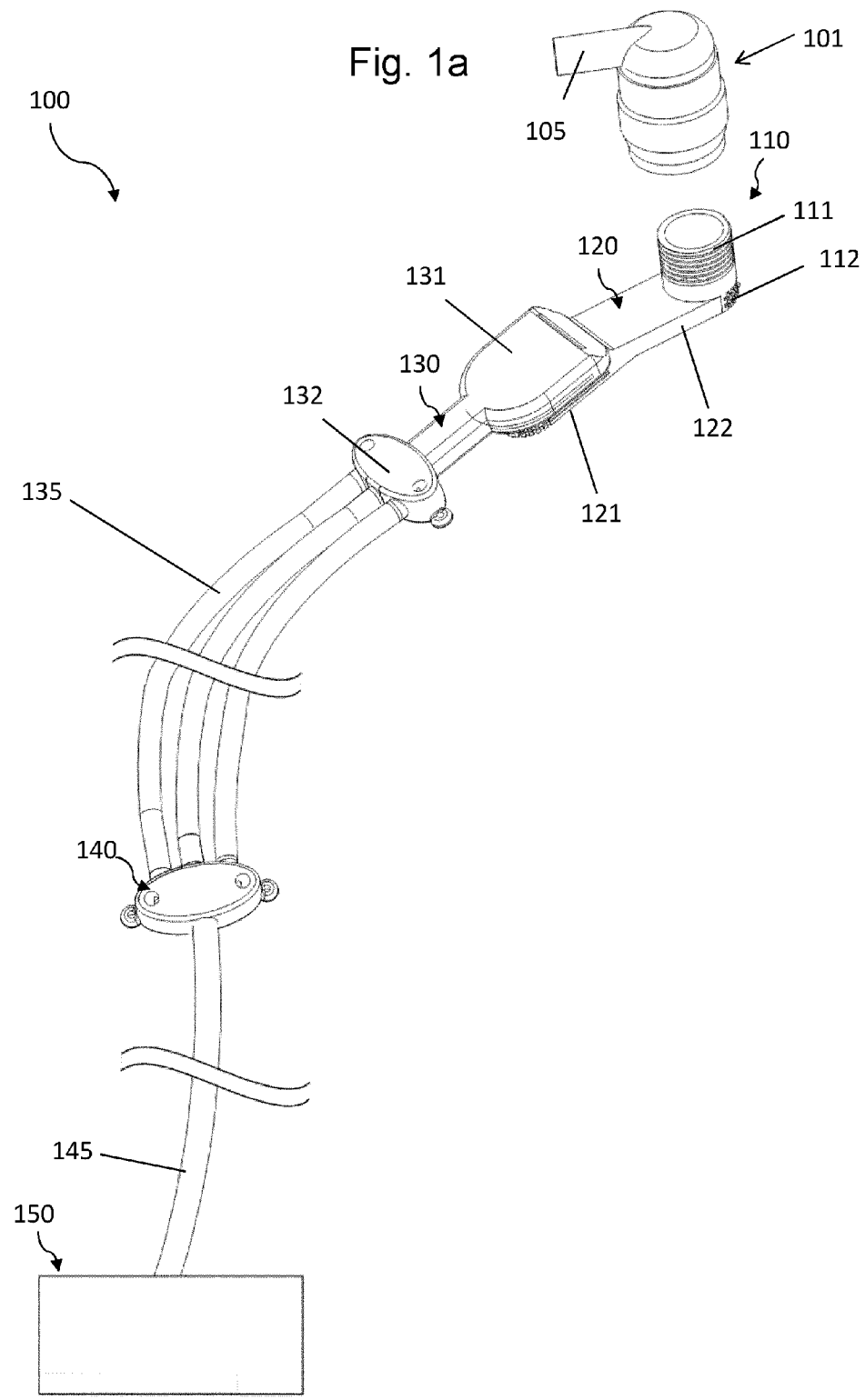
FIG. 1A illustrates a global view of a permanent percutaneous electric connection device comprising a cranial connection assembly according to a first embodiment and an intermediate thoracic connection assembly according to a first embodiment.
Figure 14:
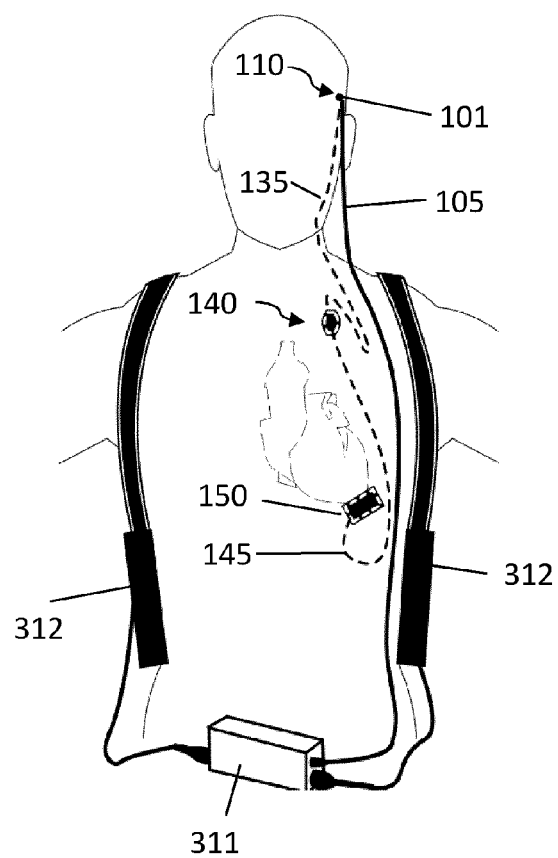
FIG. 14 is a schematic view from the front of a patient who has been implanted the permanent percutaneous electric connection device.

FIG. 14 illustrates a patient who has been implanted the permanent percutaneous electric connection device. The patient is outfit with one embodiment of the percutaneous permanent percutaneous electric connection device comprising a socket 110 protruding from the skin of the head which is connected to an internal cervical electric cable 135. The cervical cable 135 is connected to an intermediate thoracic connection assembly 140 which is connected to the implanted apparatus 150 (e.g. left ventricular assist pump) through an electric cable 145. Alternatively, the cervical cable 135 may be directly connected to the implanted apparatus 150. An external electric cable 105 plugged onto the socket 110 enables connection of the implanted apparatus 150 with external batteries 312 and an external controller 311. As illustrated in FIG. 1A, an example of a percutaneous device 100 comprises a cranial connection assembly 110, 120, 130 and an intermediate connection assembly 140, 160.

The cranial connection 110-120-130 is intended to be anchored in a cavity (L) of the skull and comprises a percutaneous socket (110) extended by an intra-osseous extension member (120), which comprises an elongated portion 122 (e.g. tubular), and an extremity (121) forming the free end of the extension member, said free end having a cup-shape, preferably oblong, which is opened outside the bone but remaining subcutaneous.

That extension member (120) extending from the percutaneous socket (110) forms a gateway element for electric connections means between an external connector provided in the socket (110) and an internal cranial connector (130).

The cranial connection assembly (110 120, 130) comprises on the one hand a percutaneous socket 110 and on the other hand a cranial electric connector (130) arranged at a distance from the percutaneous socket 110 by means of the tubular extension member 120, which is particularly advantageous. In fact, the percutaneous socket 110 is designed to be partially endosseous and osseointegrated, whereas the tubular extension (120) is designed to be totally endosseous and osseointegrated, with its free end 121 being arranged flush with the surface of the osseous structure. So, once implanted in the osseous structure, the osseous portion surrounding the extension member (120) forms an anatomical barrier reducing the risk of infectious agents propagation between the socket (110) and the electric connection element (130). The fact that the extension member 120 is designed for full osseous burial into the osseous structure with its free end being substantially flush with the surface of said osseous structure implies specific features with regard to the structure of the extension member, in particular in terms of material, shape, dimensions, etc. In particular, this means that the extension member 120 is adapted for anchoring into the osseous structure, for growth of bone around the member, etc.

Further, placing the electric connection member (130) at a distance from the socket (110) accordingly distances the electric cable (135) coupled to the internal entity (150), which limits to a maximum the risk of direct infectious contamination which could result from percutaneous passage at the level of the socket (110). Preferably, the socket (110) and the extremity (121) of the tubular intra-osseous extension member (120) are separated by a distance of at least 5 mm, preferably less than 20 mm, and preferably even of the order of 10 mm.

Preferably, the percutaneous socket (110) comprises a percutaneous abutment (111) arranged on an anchoring base (112), the percutaneous abutment (111) comprising a connector to the external entity. Connection means (such as electric wires 113) extend from the connector of the percutaneous abutment (111) up to the cranial connector provided in the electric connection member (130) through the anchoring base (112) and the extension member (120). The specific design of the socket (110) and extension member (120) enables the sub-cutaneous emergence of the electric connection means from free end of the extension member (120) for coupling with the cranial connector (130).

According to this arrangement, the intra-osseous extension member (120) and the anchoring base (112) of the percutaneous socket (110) are designed for full osseous burial in the osseous structure (these elements are therefore called intra-osseous) and are arranged such that the percutaneous abutment (111) and the extremity (121) of the tubular and intra-osseous extension (120) protrude relative to the surface of the osseous structure. According to this configuration, the socket (110), the t intra-osseous extension (120) and the extremity (121) of that extension have a general U-shape, enabling electric connections to the same side of the osseous wall, whether it is subcutaneously (especially for the electric cable in the direction of the internal entity) or percutaneously (especially for the electric connection to the external entity).

The socket (110) and the extension member (120) are angled relative to each other for enabling to bring the connection means away from the socket. Preferably, the extension portion (122) of the extension member (120) extends perpendicularly to the main axis of the socket (110). As the socket (110) and the extension member (120) are designed to be anchored in a cavity made in the cranium, these two elements are further angled relative to each other. In particular, the mean planes of the anchoring basis (112) of the socket (110) and of the extremity portion (121) of the extension member (120) (which corresponds to the mean plane of the connection member 130) preferably form an angle $\alpha$ of several degrees, which is comprised between 0.5° and 40°, preferably between 1° and 30°, and most preferably of the order of 15°. It is likewise feasible for the socket (110) and corresponding extension member (120) to have bases extending in the same plane, in particular if the osseous cavity wherein the connection assembly 110, 120, 130 must be implanted is substantially plane, or if the morphology of the patient allows it.

When the socket (110) and the extension member (120) are monobloc, i.e. made in a single piece, whether by classic machining (e.g. milling and electro-subtraction) or via additive technology (e.g. laser fusion method), then the curve of the tubular extension (120) is formed during the monobloc piece is being made. In order to be able to place the percutaneous sockets in all the patients who need a VAD placement, it is preferable to machine and realize some permanent percutaneous devices of electric connexion, which are angled at an angle comprised between 0.5° to 40° or which bases extend in the same plane.

This particular configuration of the cranial connection assembly (110, 120, 130) confers on the socket 110 the same guarantees as a conventional extra-oral implant (bone anchorage hearing aid and prosthetics supports) composed of an implant fixed to a bone attached to a percutaneous abutment. The risks of infection, and more precisely the risks of propagation of the infection to the electric power cable, and therefore to the internal entity (150), are almost zero, especially due to the reduction in surrounding soft tissue ("soft tissue reduction") at the level of the percutaneous passage.

In fact, the present cranial connection assembly (110, 120, 130) may be implanted with respect to the founding principles of extra-oral implantology by proceeding with implantation according to two successive operations. In the first place, the intra- and juxtaosseous part of the cranial connection assembly should be out in place (comprising the base (112) of the socket (110), of its extension (120), and the electric connection member (130), these pieces forming a monobloc assembly), then the cutaneous plane should be closed again. Over a few months, osseous cicatrisation occurs around this implant, or osseointegration during the feeding phase of the implant. Second, three to four months after insertion of the implant, the percutaneous electric connection can be made by placing the abutment (111) of the socket (110) through the dermal plane while proceeding with the reduction of surrounding soft tissue.

Alternatively or preferentially for some cardio-thoracic surgeons, if the second operation cannot be differed, it is possible to place the cranial connexion assembly and the reduction of the surrounding soft tissues during the same surgical intervention. The abutment (111), percutaneous part of the socket (110), and being a monobloc element, is then placed through the cutaneous plan and positioned in the cavity made in the recipient bone during the same intervention. At the end of the intervention, the preparation of the site of the recipient bone should anatomically offer the same conditions as those during the installation of a permanent percutaneous device of electric connection, that is to say, in two successive surgical periods. In such case, the device is implanted in one session.

Preferably, the surgical procedure includes a prior preparation step for accurate identification of the implantation site by superimposition of optical and radiological images of the ideal position of the permanent percutaneous device of electric connection.

Once that connection is perfectly set up, the surgeon makes an arcuate or a linear incision but that incision could possibly be bicoronal as what is realized for a complete skin detachment of the hemiscalp.

The abutment (111) is provided for connection of an external plug (101) prolonged by an electric cable (105) connected to the external apparatus, for example a power generator.

For the placing of the permanent percutaneous device of electric connection (110, 120, 130), the implantation method such as described in US patent application registered on Dec. 4, 2009 under number U.S. Ser. No. 12/631,161 could be possibly a source of inspiration regarding the first surgical period. In particular according to this implantation method, the first surgery comprises the following successive steps:

preparation step of the receiving osseous site, during which:
  the cutaneous plane opposite the receiving osseous site is incised, then
  the periosteum of the receiving osseous site is incised and unstuck, then pushed back to disengage the osseous structure, then
  the osseous structure is hollowed out to form a cavity in which the plate-implant (comprising the base (112) of the socket (110), and the extension member 120) must be anchored;
anchoring step of the plate-implant in the cavity formed in the receiving osseous site, during which:
  the plate-implant is positioned and stabilised in the cavity formed in the receiving osseous site, to obtain excellent primary stabilisation, favourable to osseointegration of the implant,
  then preferably:
    osseous fragments are placed on the plate-implant to cover it over, with the exception of the fixed port of electric connection, then
    said osseous fragments are covered with a membrane to keep the osseous fragments in position to ensure guided osseous regeneration, said membrane being fixed to the osseous structure on the one hand and to the plate-implant on the other hand to keep the osseous fragments in position.

Figure 3:
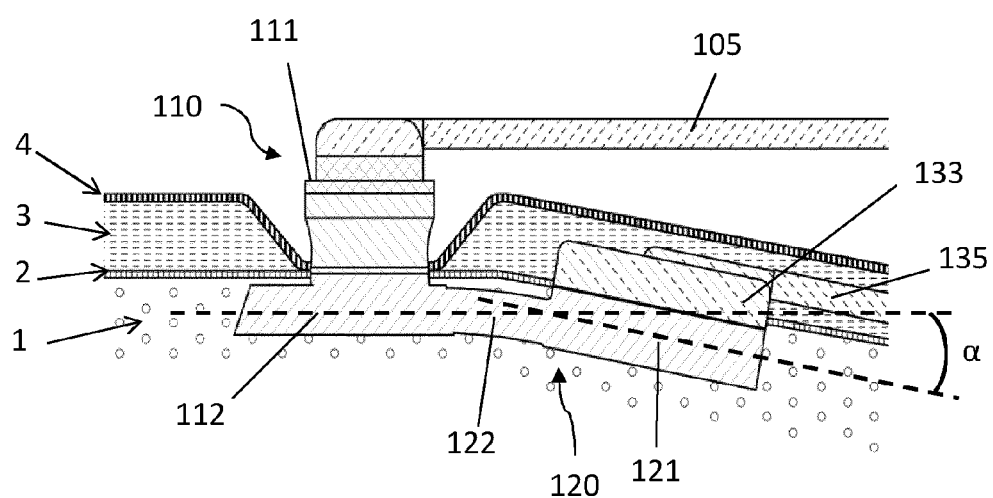
FIG. 3 illustrates a sectional view of a cranial connection assembly implanted in an osseous wall.

As shown in FIG. 3, the particular structure of the cranial connection assembly (110, 120, 130) has the advantage of being able to be anchored fully in the osseous cavity 1 by limiting the elements not covered by osseous proliferation. So, at the level of the socket 110, only the connection port of the base 112 of the socket 110 projects relative to the osseous wall 1 and to the periosteum 2. It is at this level that reduction in soft tissue is made (the dermis 3 is removed, and the epidermis 4 is plated and sutured directly on the periosteum 2) limiting proliferation of infection due to percutaneous passage. Further, the fact that the oblong cup-shaped extremity (121), of the tubular extension (120) emerges from the osseous plane at a distance from the socket (110), where reduction in surrounding soft tissue has been made, further reduces the risk of contamination at the level of the connection cable 135.

The tubular extension (120) of the socket (110), which extremity (121) forms an oblong cup from which the electric connecting means (113) can emerge from the socket (110) to the cranial connector (130), due to its functionalities, characterises the innovative aspect of the device; in the prior art, there is no systematised possibility for realizing a removable-irremovable electric connection means for attaching safely a cable internal to the organism to equipment external to this same organism on exit from a trajectory in the thickness of the bone.

According to the proposed implantation, the cranial connection assembly (110, 120, 130) is implanted so that the tubular extension 120 is fully endosseous, that is, fully covered by the bone after implantation. The socket 110 is partially endosseous only and osseointegrated since the percutaneous abutment 111 must be able to pass through the skin while being monobloc with the anchoring base 112 at the same time. The connecting means of the electric cable 135 are placed on the cranial connector located in the electric connection member (130) positioned at a non-zero distance, ideally of the order of 15 to 20 mm of the emerging at the extremity 121 of the tubular extension 120 of the socket 110. In this way, the oblong cup-shaped extremity 121 of the tubular extension 120 is partially subcutaneous, allowing the emerging of the electric connecting means 113 between the socket 110 and the cranial connector 130, this latest ensuring the connection to the electric cable 135 to the internal unit 150.

As indicated earlier, the existing distance between the oblong cup-shaped extremity 122 of the tubular extension 120 and the socket 110 limits any contamination coming from the percutaneous passage. This "distance" arrangement of the cranial connection assembly 110, 120, 130, likewise creates better reduction of soft tissue without being impeded by the electric connection cable 135 which must end up subcutaneously to the internal entity 150.

For the surgeon to perform a soft tissue reduction around the abutment of the socket, no implanted element (e.g. either screws head or connecting means) must emerge from the bone or cover the bone in a surrounding radius of 5 mm to 10 mm. With the proposed arrangement, soft tissue reduction is possible because the electric connection wires are brought away from the socket 110 through the osseous structure thanks to the extension member 120. Indeed, the tubular extension member is designed to emerge from the bone and be distant from the abutment of the socket, preferably by a distance of at least 5 mm.

A great advantage conveyed by the proposed arrangement of the percutaneous connection device is that it enables at the same time the two antinomic requirements of allowing a soft tissue reduction and allowing changing of the cervical cable.

As mentioned above, there is preferably provided an intermediate connection assembly 140, 160 which comprises an intermediate electric connection element 140 for making an electric connection between the cranial connection assembly 110, 120, 130 and the internal entity 150.

Figure 1B:
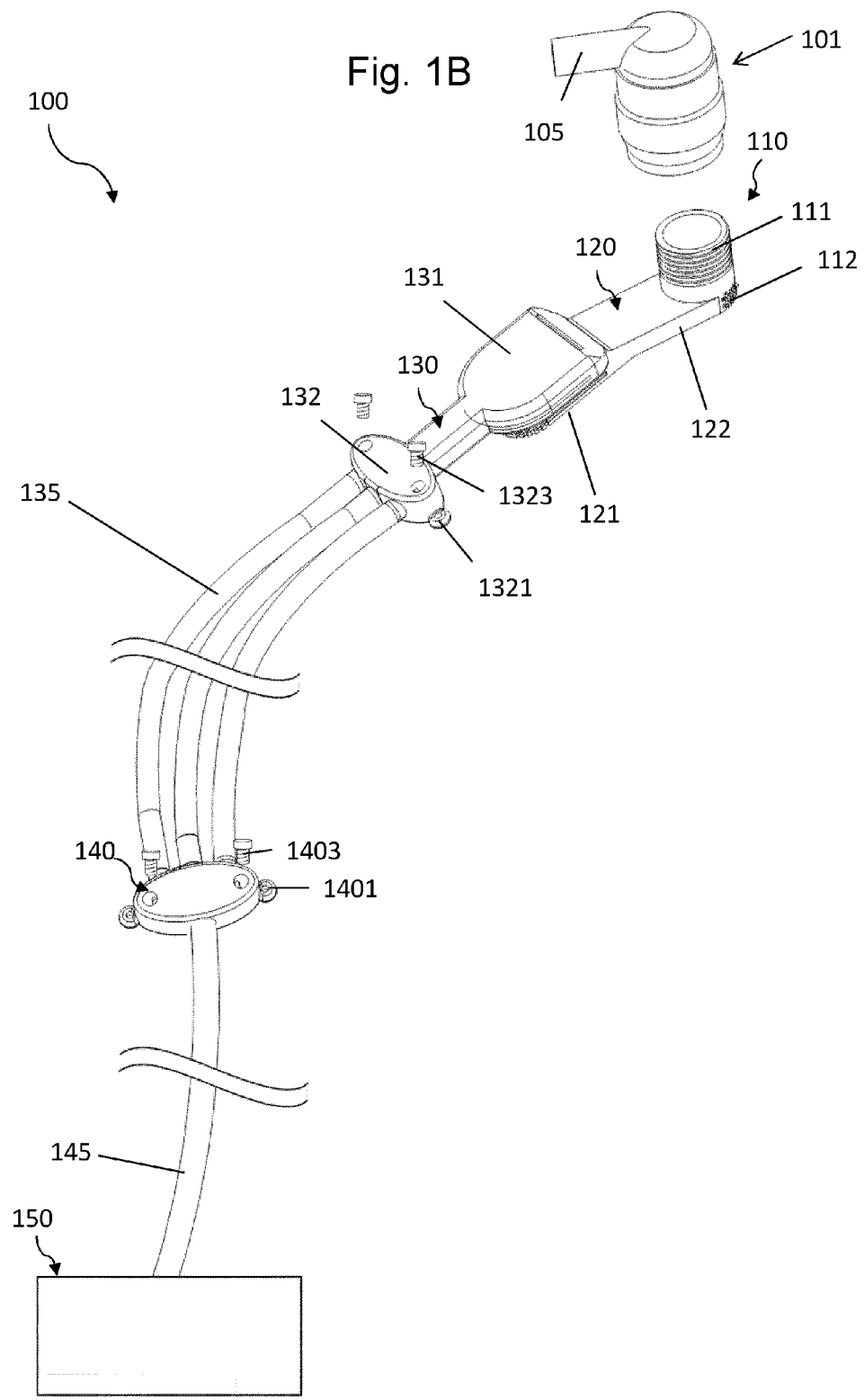
FIG. 1B illustrates the means to lock the connection assembly of the device of FIG. 1A.
Figure 1C:
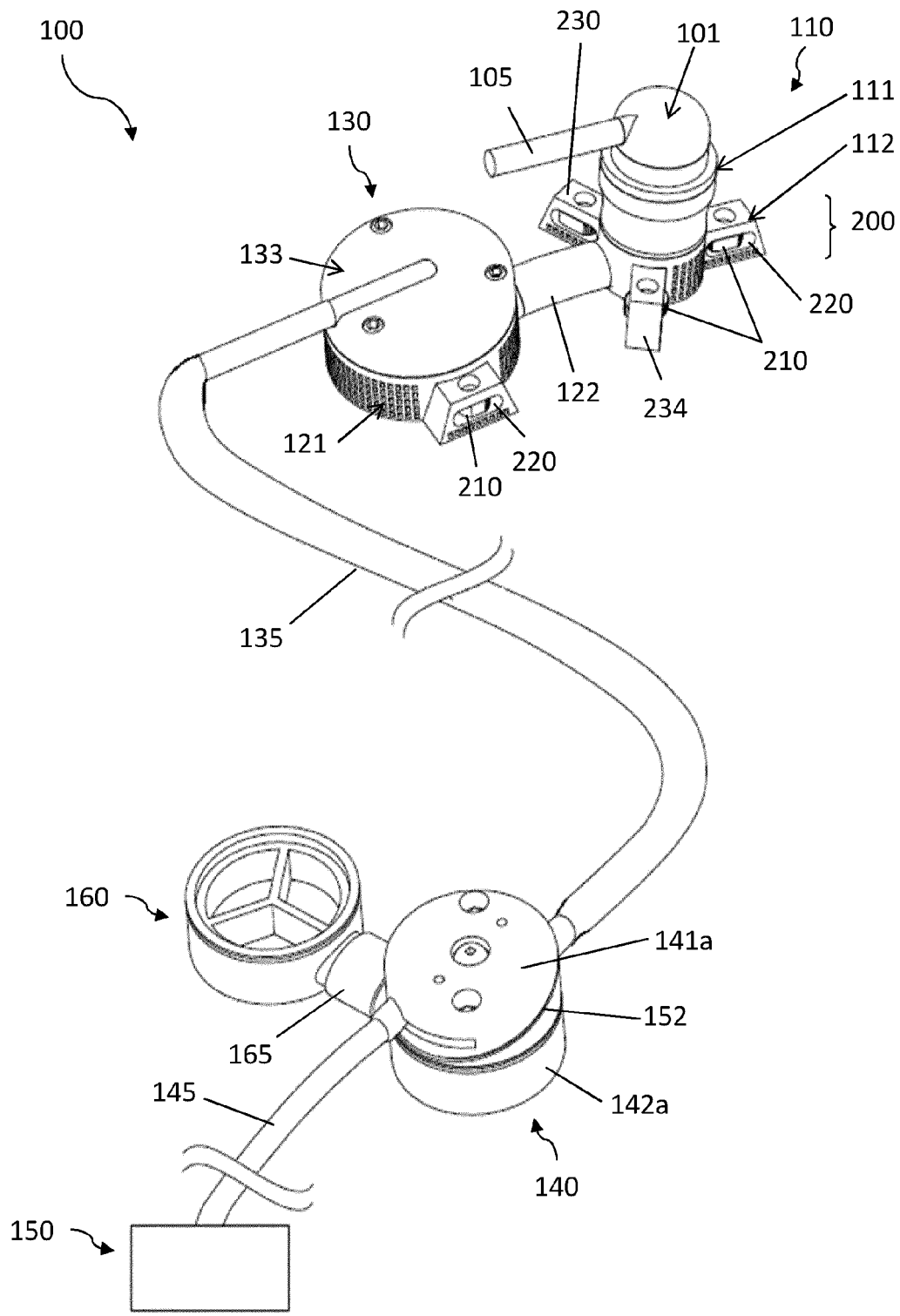
FIG. 1C illustrates a global view of a permanent percutaneous electric connection device comprising a cranial connection assembly according to a second embodiment and an intermediate connection assembly according to a second embodiment.

Preferably but non limiting, the intermediate connection assembly 140, 160 further comprises an auxiliary socket 160 connected to the intermediate electric connection element 140 by means of an intermediate connecting element 165 creating an electric link between the element 140 and the auxiliary socket 160 (see FIG. 1C). Such auxiliary socket 160 may be adapted to be connected to an emergency external power supply to maintain power supply to the internal entity 150, and this can be very advantageous for a VAD or TAH or other types of internal entities. This auxiliary socket 160 can for example be designed according to the idea of PCT application published under the reference WO 2010/122 142. Not only is this auxiliary socket 160 used during replacement of the electric cable 135, but it can likewise be used in case of failure of the main power supply via the cranial connection assembly 110, 120, 130. Once the cable 135 is replaced by a new one and the cranial connection assembly 110, 120, 130 is operational, it suffices to restore supply to the internal entity 150 by means of the cranial connection assembly 110, 120, 130 and to disconnect the auxiliary power supply of the auxiliary socket 160.

It should be noted that in a simplified version, this intermediate connection assembly could be limited to a device of direct connection type by way of a "simple" connecting socket (see FIGS. 1A and 1B).

The cranial electric connection 130 and the intermediate electric connection element 140 are both connected via an electric cable 135, preferably removably mounted.

In addition, the intermediate electric connection element 140 allows the connection, at the outlet, of the permanent cable 145 coming from the internal entity 150, especially to supply electric power. The intermediate electric connection element 140 is preferably fitted with the interfacing corresponding to the feed wires of various types of internal entities to be able to attach it to any type of internal entities.

In the case where the internal entity 150 to be supplied with power is a circulatory assistance apparatus of type VAD or total artificial heart TAH, the intermediate electric connection element 140 can be positioned at the level of the thorax, preferably close to the sternum, such that it is qualified as an electric thoracic connector 140 whereas the electric connector 130 is qualified as an electric cranial connector.

Due to this particular arrangement of the cranial connection assembly (110, 120, 130) and of the intermediate connection assembly (140), the connection of the percutaneous socket 110 to an external power supply (generator, battery, etc.) by means of an electric cable 105 electrically powers the internal entity 150, of VAD or TAH type, by means of two electric connection elements 130 and 140 and associated cables 135, 145. This arrangement could likewise be used to transfer information between the internal apparatus 150 and an external apparatus, since it suffices in this case to adapt the electric connection cables and their interfacing.

Employing the intermediate connection assembly 140 is optional but does improve the reliability of the device 100. In fact, the power supply part, located between the electric cranial connector 130 and the electric thoracic connector 140 is highly stressed during the patient's movements, especially at the level of the neck, which accelerates wear and makes it more fragile. The power supply part, located between the electric thoracic connector 140, which can be implanted near the sternum, and the internal entity 150 as such undergoes minimal stress. Adding an electric thoracic connector creates a buffer, and limits the risks of untimely disconnection which could harm the patient, in particular when the internal entity 150 is a VAD or a TAH.

In addition, it may prove necessary to change the electric cable 135 connecting the electric cranial connector 130 to the electric thoracic connector 140 especially because of its wear due to movements made by the patient. Using the intermediate connections assembly 130, 140 makes this change of electric cable easier, especially in that it enables the structure of the internal entity 150 of VAD or TAH type not to be modified, and can likewise guarantee operation of this VAD during changing of cable.

In addition, the electric cable 135 connecting the two electric connection elements 130,140 is preferably set up removably on both connectors 130 and 140, so that it can easily be replaced at any time and without difficulty. To do this, specific connectors adapted for this detachable capacity, such as for example those described herein below, and are made in the electric connection elements 130 and 140.

Moreover, for easy replacement of the electric cable 135, the latter has an external envelope preferably made of material adapted to limit hooking of foreign bodies. Typically, this external envelope is made of silicone, Teflon or Dacron, or any other material adapted to the medical field and having undergone chemical and/or mechanical treatment adapted to limit adherence of tissue, etc. The wires will be preferably made of a biocompatible material such as the metal alloys used for pacemaker leads.

In order to limit the thickness of the cervical cable 135, it can be split into multiple cables preferably two or three as illustrated in FIG. 1A.

A first embodiment of the connection assembly 130 and 140 will now be described in greater detail in relation to FIGS. 11A to 11F.

Figure 11A:
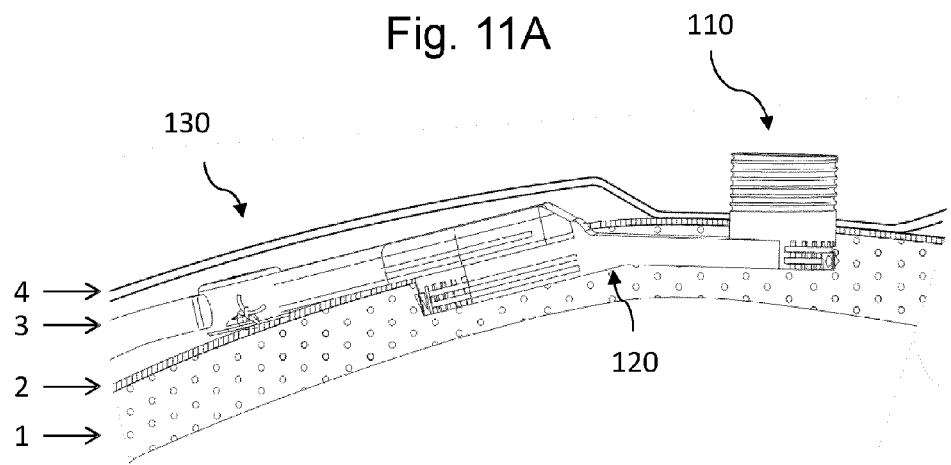
FIG. 11A illustrates a cranial connection assembly with the extension member and part of the socket buried in the osseous structure.
Figure 11B:
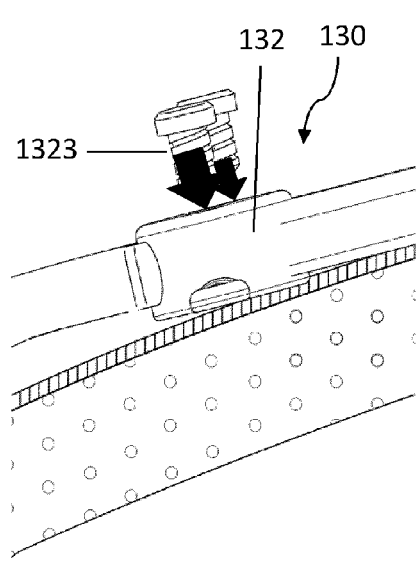
FIG. 11B illustrates an embodiment of the locking means (screw) to inserted in the subcutaneous cranial connecting element.
Figure 11C:
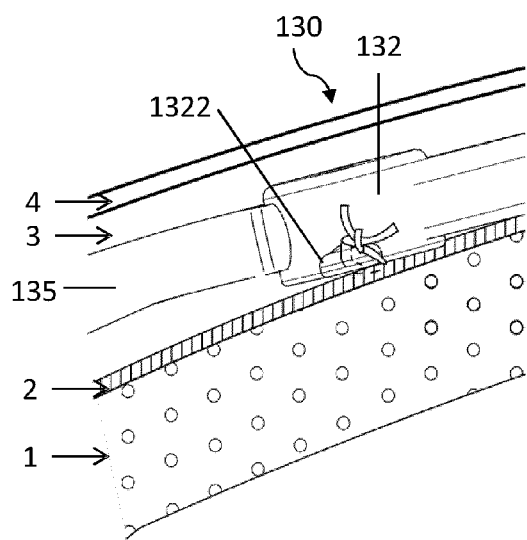
FIG. 11C illustrates a first embodiment of the subcutaneous cranial connecting element being sutured to the periosteum.
Figure 11D:
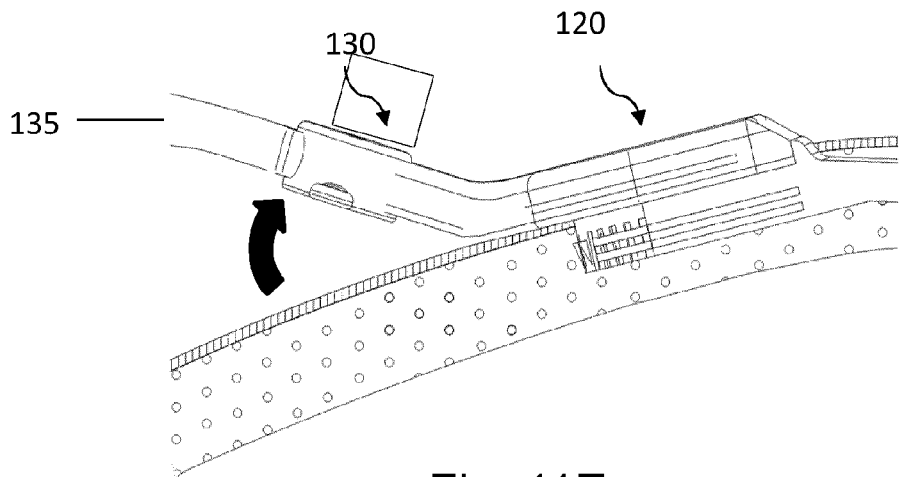
FIG. 11D illustrates the cranial subcutaneous cranial connecting element being lifted, as the first step to change the cervical cable.
Figure 11E:
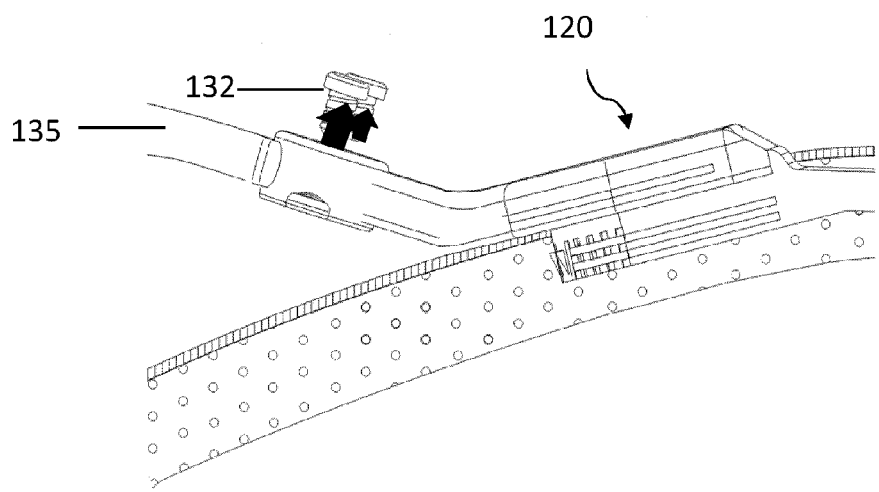
FIG. 11E illustrates the locking means of the subcutaneous cranial connecting element being removed, as the second step to change the cervical cable.
Figure 11F:
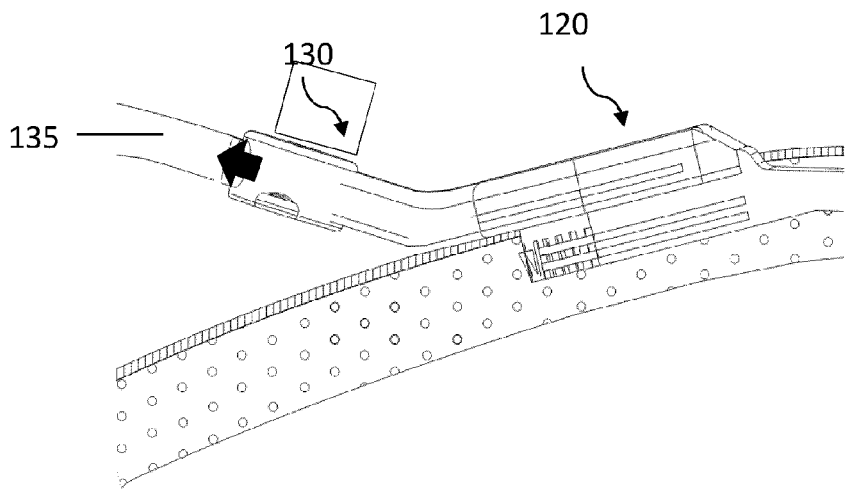
FIG. 11F Illustrates an intermediate connecting cable removed from the subcutaneous cranial connecting element in order to proceed to a replacement of an intermediate connecting element.
Figure 12:
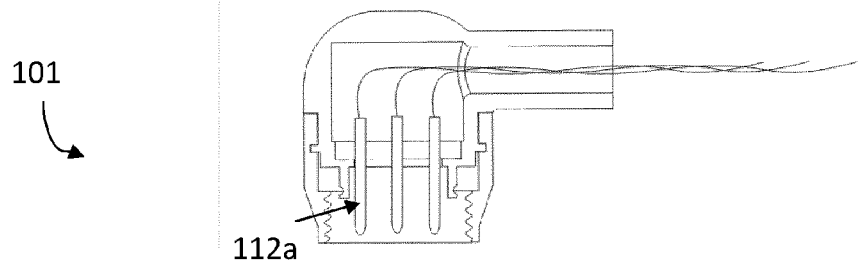
FIG. 12 illustrates a cross-section view of one embodiment of the external plug comprising multiple contacts (112a) and electrical wires (113) to fit into the socket of the cranial connection assembly.
Figure 13:
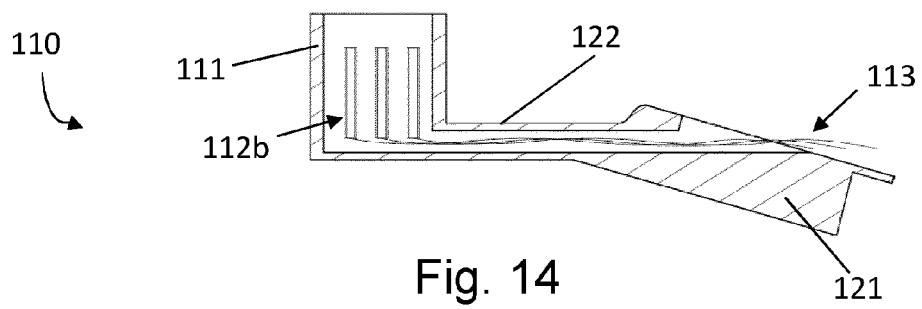
FIG. 13 illustrates a cross-section view of the percutaneous connector, which comprises multiple contacts (112b) and electrical wires (113).

The connection assemblies 130, 140 are connected with the cervical cable 135 which is outfitted with connectors at is extremities. Alternatively, the cable 135 could be outfitted at its extremity with coils or any element that can convey energy to another part. In other to maintain the cable 135 and the connection assemblies 130, 140 connected, the connection assemblies 130, 140 include each two internal thread paired with screws. The connection assemblies additionally include seals to ensure that no liquids will enter in contact with the connectors. The connection assemblies 130, 140 comprise eyelets 1322, 1422 on each side. These eyelets allow suturing the intermediate connection assemblies 130, 140 to anatomic tissues. The cranial intermediate electric connection element 132 is sutured to the periosteum 2 as shown in FIG. 11C. The thoracic intermediate connection assembly can in a similar fashion be suture to a fascia or any other anatomic tissue.

We will now describe more precisely the first embodiment of the cranial intermediate connection assembly 130, also called the electric connection member 130.

In this embodiment, the electric connection member (130) comprises an extra-osseous electric connection element (132) provided with the cranial connector, and a flexible intermediate element (131) for bringing the connection means from the extension member (120) to the extra-osseous electric connection element (132), wherein the flexible intermediate element (131) is securely fastened to the free end of the extension member (120) on the one hand and to the extra-osseous electric connection element (132) on the other hand.

Preferably, the flexible intermediate element (131) is overmold onto the free end of the extension member (120) and/or onto the extra-osseous electric connection element (132) and around the electrical wires 113. Preferably the overmold is made in silicone or with silicone or any other material that is both flexible and biocompatible. The flexibility of the overmold will allow lifting the subcutaneous connector and to set it in an ad hoc surgical field, thus facilitating the replacement of the cervical cable.

Figure 9A:
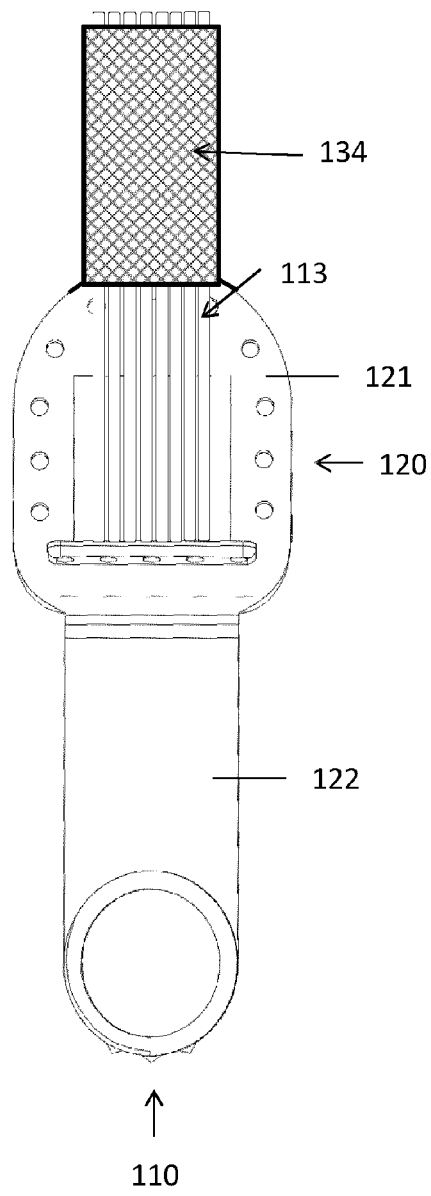
FIG. 9A illustrates part of the cranial connection assembly of FIG. 1A with a ribbon cable escaping from the extension member, wherein said ribbon cable is protected by a textile structure fixed on the extension member.
Figure 9B:
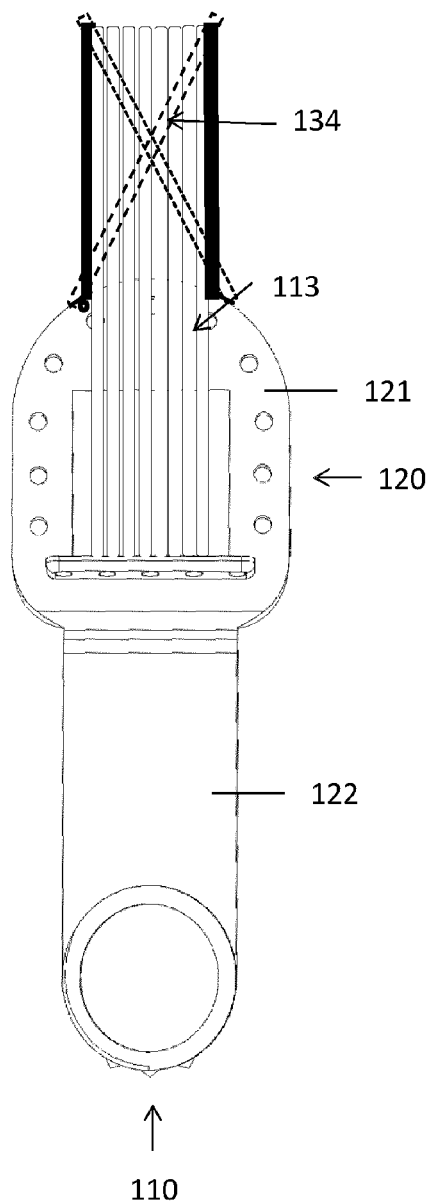
FIG. 9B illustrates part of the cranial connection assembly of FIG. 1A with a ribbon cable escaping from the extension member, wherein said ribbon cable is protected by a structure made of textile or titanium.
Figure 9C:
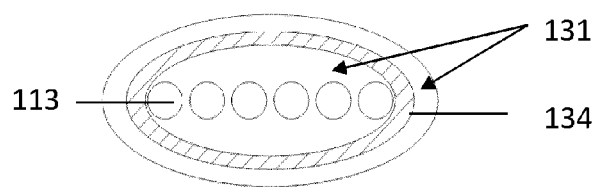
FIG. 9C illustrates a cross section view of the ribbon cable, wherein the electric connection means are surrounded by a relief structure made of textile or titanium and overmold in a flexible material such as silicone.
Figure 10:
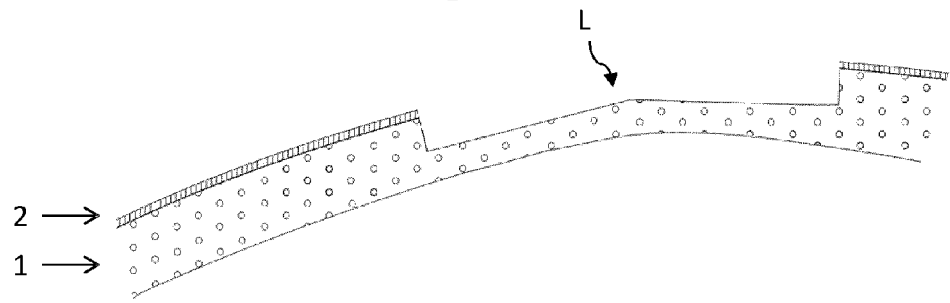
FIG. 10 illustrates a sectional view of the implantation site where a cavity (L) has been made in the osseous structure.

Preferably, the flexible intermediate element (131) comprises a mechanical relief system (134) such as a titanium structure (titanium wires grid osseous implant, titanium grid) or any textile structure such as illustrated in FIGS. 9A, 9B, 9C. Such relief system is adapted for preventing elongation of the connection means (i.e. the wires 113) along their longitudinal axis. The relief system (134) may comprise a frame of titanium wire and/or a cord of textile material within the ribbon cable in order to protect the electric wires from the potential mechanical strains.

In order to mechanically lock and seal the electric connection element 132, the subcutaneous connector is preferably be equipped with a screw or pin system 1321.

If the cervical cable 135 needs to be changed, then the surgeons first unscrew the screws 1323 than are used to secure the electric connection element (132) onto the osseous surface. The flexible intermediate element (131) can then be lifted (see FIGS. 11D and 11E) and the cervical cable 135 can thus be changed without contamination of the connector of the electric connection element 132. Indeed, the fact the electric connection element 132 can be lifted enables isolating it from the operating field.

Alternatively, the electric connection member 130 may comprise an extra-osseous lid (133) adapted to be securely fastened onto the free end (122) of the extension member (120), wherein the second connector is arranged within said extra-osseous lid (133). Such embodiment is illustrated through FIGS. 1C, 2A, 2B, 2C, 2D, and 2E.

Another embodiment of the electric connection devices 130 and 140 will now be described in greater detail in relation to FIG. 6A. The electric connection device illustrated in FIGS. 6A and 6B correspond to the thoracic electric connecting device 140 but the corresponding teaching is similar for its use in the cranial electric connecting device 130.

The lid 141a of the intermediate electric connection device 140 acts as such to allow detachable connection of the electric cables to the intermediate electric connection element 140, especially the detachable connection of the electric cable 135. It comprises a first connector 143a, adapted to receive the electric cable 135 originating from the cranial connecting device 120, and a second connector 143b, adapted to receive the electric cable 145 coupled to the internal entity 150 of VAD or TAH type.

Of course, the structure of the intermediate electric connection element 140 described here is not limiting. Typically, it is possible to place the transmission and connection means in the base 142a.

Each connection device 143a, 143b comprises:
An inlet orifice 144 of general cylindrical form, and
A blockage system 146 of the electric cable 135, 145 in the inlet orifice 144.

The blockage system 146 of the cable 135, 145 can especially be formed by a cam 147a arranged inside a housing 147b terminating radially relative to the inlet orifice 144. The cam 147a is mobile in rotation about an axis of rotation (orthogonal relative to the direction of insertion of the cable 135, 145 in the inlet orifice 144) between a blocking position, in which the cam 147a projects in the inlet orifice 144 to compress the cable 135, 145 and keep it fixed, and a release position, in which the cam 147a is substantially confined in the housing 147b and does not enter the inlet orifice 144, the cable 135, 145 then being able to be moved freely.

To shift the cam 147a from one position to the other, the blockage system 146 further comprises a through orifice 148b on an upper face, adapted to cooperate with an actuation element 148a arranged on an upper face of the cam 147a. The hole 148b and the actuation element 148a are arranged according to the axis of rotation of the cam 147a.

Figure 6A:
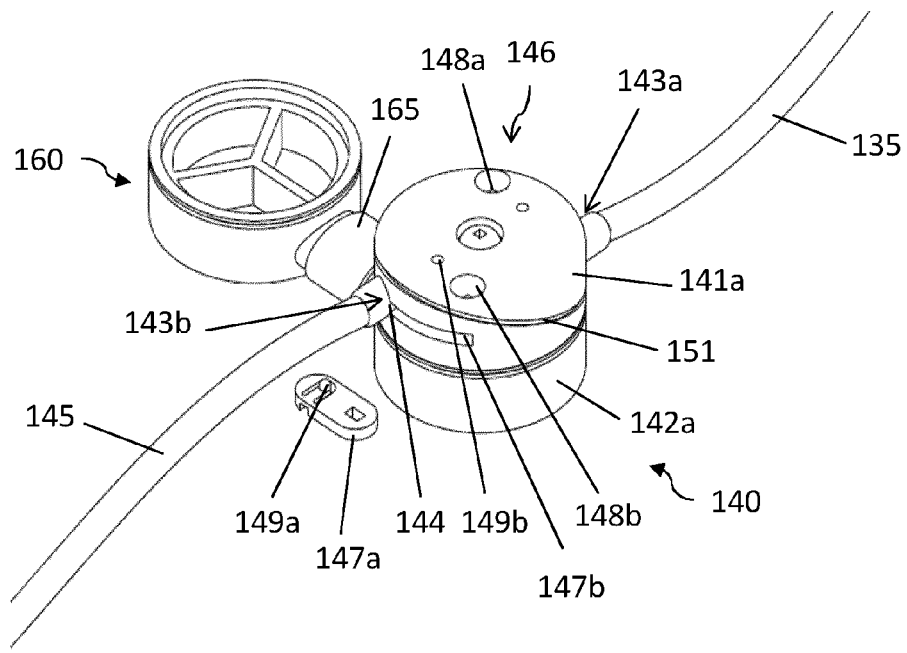
FIG. 6A illustrates an intermediate thoracic connection assembly according to a third embodiment.

In the embodiment illustrated in FIG. 6A, the actuation element 148a is a square pivot extending from the upper face of the cam 147a in the hole 148b. Rotation of the pivot using a key of adapted shape introduced into the hole turns the cam 147a and therefore fixes or frees the cable 135, 145.

As a variant, the pivot 148a has another form, such as for example a polygonal form, a star shape or any other geometric form enabling simple actuation with a key or automatically.

According to yet another variant, the actuation element 148a is a rectilinear groove (or two rectilinear grooves crossed perpendicularly), hollowed in the upper surface of the cam 147a. In this variant embodiment, the cam 147a further comprises a rod extending from the lower surface of the cam 147a along the axis of rotation, and protruding in the lower face of the housing 147b to block the cam 147a inside said housing 147b during its rotation. The rotation of the cam 147a can be made due to a screwdriver of form complementary to the actuation element 148a.

The form of the cam 147a is adapted to progressively enter the inlet orifice 144 when the latter is rotated by an appropriate tool about its axis of rotation in the direction of insertion of the cable in the inlet orifice 144. In this way, the cam 147a exerts a progressive compression force on the cable which is inserted in the inlet orifice 144, and keeps it in position. Moreover, this pressure of the cam on the cable advances the latter slightly into the inlet orifice 144, improving the seal of this connection.

For example, the cam 147a can have a divergent form in the direction of insertion of the cable and/or the axis of rotation of the cam 147a can be eccentric relative to its centre of symmetry as illustrated in FIG. 6A.

According to a preferred embodiment, the blockage system 146 further comprises protection means of the cable to prevent the latter from being crushed by the cam 147a in the blocking position by limiting the compression forces exerted on the cable, and locking means of the cam 147a in the blocking position.

The protection means can especially be constituted by a stop, designed to limit the course of the cam 147a. The stop can be placed for example in the housing, or limit movement of the actuation element. The position of the stop is selected such that in the blocking position the cable is blocked in the inlet orifice 144, without as such being too compressed.

The locking means of the cam 147a can be constituted as such by a system adapted to block rotation of the cam 147a once the latter is in the blocking position.

In the embodiment illustrated in FIG. 6A, the protection means and the locking means are formed by a single system, specifically here a locking pin 149a protruding from an upper surface of the cam 147a, and adapted to be inserted forcefully into a terminating locking orifice 149b made in an upper part of the lid 141a such that the pin 149a is accessible from the exterior when the latter enters the orifice 149b.

The orifice 149b and the locking pin 149a are arranged such that the pin 149a is opposite the orifice 149b when the cam 147a is in the blocking position.

Advantageously, the pin 149a automatically enters the orifice 149b when the latter are opposite each other. For this, the pin 149a can for example comprise a flange protruding in the direction of the orifice 149a from a free end of an elastic strip which extends above a cavity made in the upper face of the cam 147a.

The strip is preferably selected so that when at rest it is flush with the upper face of the cam and the flange projects beyond the cavity. In addition, the arrangement and the dimensions of the cam 147a and of the housing 147b are selected such that in the release position of the cam 147a the distance between the upper surface of the cam 147a and the upper face of the housing 147b is less than the height of the flange. Similarly, in the release position, the flange is stressed by the upper surface of the housing 148a to enter the cavity, while in the blocking position it projects out of the cavity, through the locking orifice 149b.

In this way, when the electric cable 135, 145 is inserted in the inlet 144 the actuation of the pivot 148a via an appropriate tool rotates the cam 147a and makes it progressively enter the inlet of connection 144, until it is in the blocking position and compresses the cable 125 or 145, in which the pin 149a is opposite the locking orifice 149b and prevents any additional movement of the cam 147a. The cam 147a is itself blocked in this position, and can neither free the cable nor compress it any more.

To withdraw the cable 135, 145 from the inlet 144, it suffices to press on the pin 149a via the orifice 149b to push it back into the cavity and set the cam 147a in rotation in the direction of release of the cable 135, 145, then withdraw the cable from the inlet 144.

As a variant, the protection and locking means can likewise be a sliding element as per the organ described in PCT application published under reference WO 2010/122140.

To improve blockage of the cable 135, 145 in the inlet 144, the form of the inlet can be bevelled, whereas the end of the cable 135, 145 is cylindrical in revolution. As a variant, the end of the cable 135, 145 can be bevelled at the level of contact with the cam.

In addition, the cam can further exhibit surface irregularities, such as flutes, teeth, rough spots to increase friction with the cable 135, 145 and accordingly improve its blocking.

Besides, as is illustrated in FIG. 6A, the intermediate electric connection element 140 can be fitted with at least one groove 151, made for example on the lid 141a of the connection element 140. The purpose of this groove 151 is to fix a dam 141b designed to insulate one of the insertion orifices 144 from the cable 135, 145 when the latter has to be changed.

Preferably, the insulation dam 141b has a tapered form designed to be clipped on to the groove 151. More preferably, the groove 151 is inclined relative to the mean plane of the lid 133, so as to pass below one of the two orifices 144 and above the second of the two orifices 144. According to this configuration, the dam 141b fully insulates the orifice 144 for which the cable must be changed, which prevents elements originating from the body of the patient from being inserted into the orifice 144 during changing of the cable.

Figure 6B:
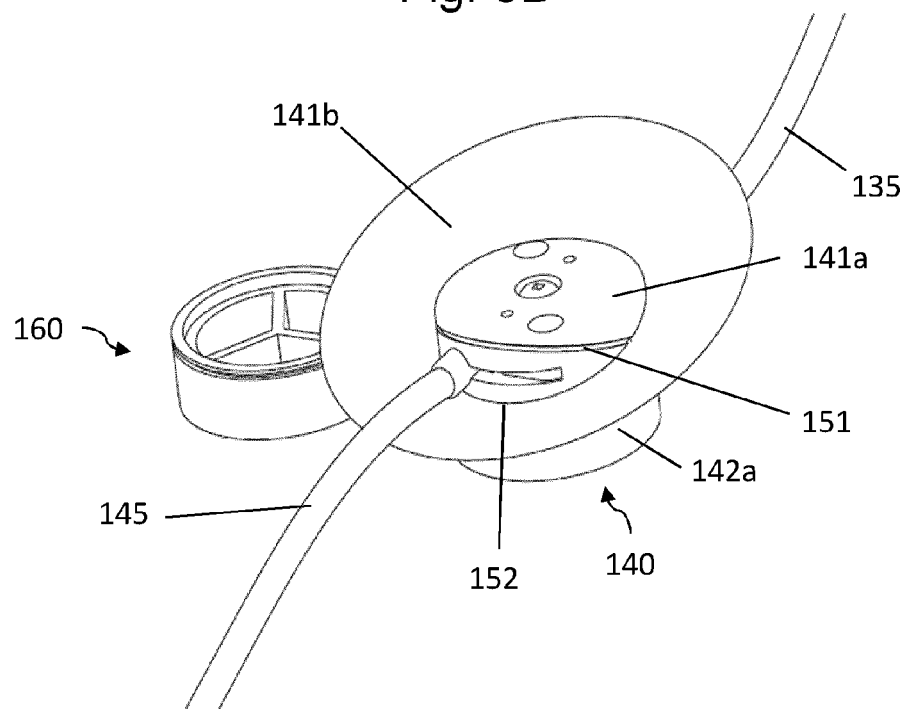
FIG. 6B illustrates an intermediate connection assembly according to a third embodiment, with an insulation dam.
Figure 7A:
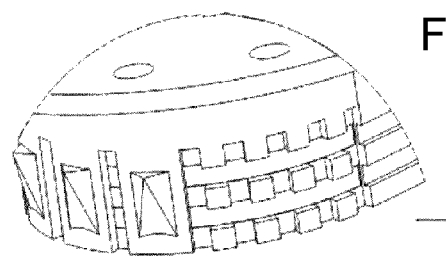
FIGS. 7A and 7B illustrate a first embodiment of the percutaneous endosseous connector of the first embodiment of the cranial connection assembly with a first embodiment of the anchoring system, which is particularly adapted for subtractive manufacturing methods.
Figure 7A:
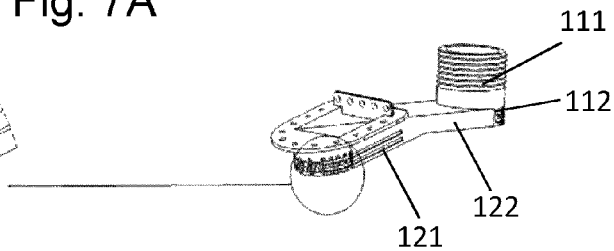
Figure 7B:
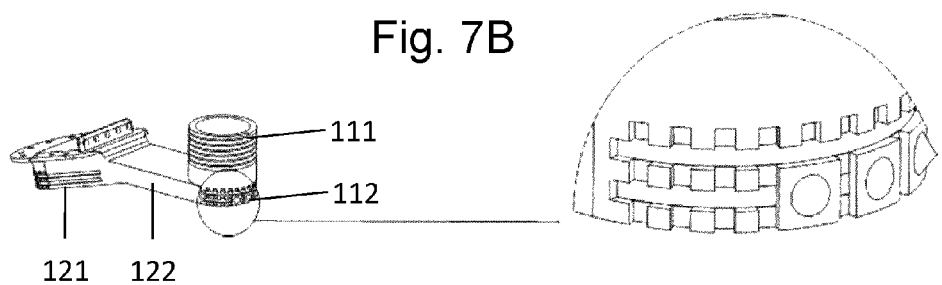
Figure 7C:
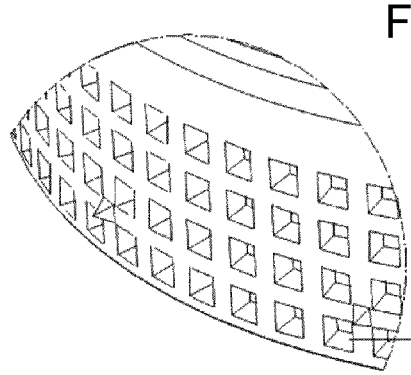
FIGS. 7C and 7D illustrate a second embodiment of the percutaneous endosseous connector of the first embodiment of the cranial connection assembly and a second embodiment of the anchoring system, which is particularly adapted for additive manufacturing methods.
Figure 7C:
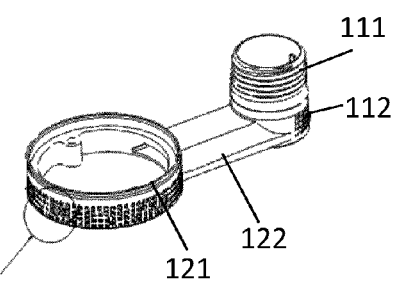
Figure 7D:
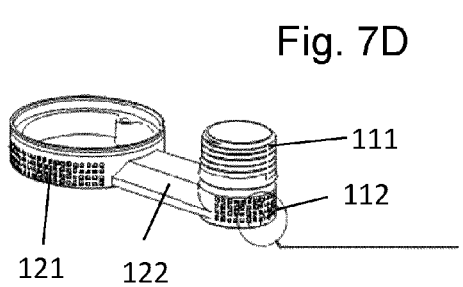
Figure 7D:
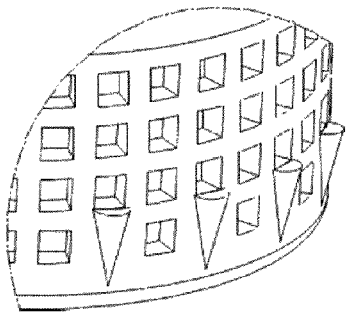

Preferably, as illustrated in FIG. 6B, the element 140 comprises two grooves 151, 152 arranged crossed relative to each other, the groove 151 being provided for fixing the dam 141b when the cable 135 connected to the cranial connection assembly 110, 120, 130 must be disconnected and replaced, and the groove 152 is provided to fix the dam 141b when the cable 145 connected to the internal device 150 must be disconnected and replaced.

FIG. 6A illustrates the case where only the groove 151 insulating the orifice 144 during replacement of the cable 135 is provided on the intermediate electric connection element 140. It could also be that only the groove 152 insulating the orifice 144 during replacement of the cable 145 is provided on the intermediate electric connection element 140 as illustrated in FIG. 1C.

In reference to the attached figures, a first embodiment of an intra-osseous anchoring system 200 according to the invention will now be described in its application to the permanent percutaneous connection device 100 when used in a power transmission system for instance.

This application of the anchoring system 200 according to the invention is in no way limiting to the extent where such a system can be adapted to any device requiring intra-osseous anchoring, such as prostheses support apparatus of limbs, for example.

As has been explained earlier, the cranial connection assembly 110, 120, 130 must be positioned and stabilised in a cavity L made in the thickness of the skull of the patient.

The cavity L consists of an orifice having a bottom and internal lateral walls, and the dimensions and form of which are adapted to the dimensions and form of the assembly such that it can accommodate it with slight friction to be able to hold it, at least temporarily.

To keep the cranial connection assembly fixed in position in the cranium, the base of the socket 110 and of the extension member 120 are both fitted with intra-osseous anchoring systems 200 adapted to anchor them to the internal walls of said cavity L.

The anchoring system 200 of the socket 110 comprises an anchoring element 210 arranged inside an opening 220 made in part of the socket which is inserted in the cavity L.

According to a first embodiment, the anchoring system 200 comprises several openings 220, preferably at least three, each made in a corresponding arm 230 extending radially from the socket 110. The cavity L has a complementary "star" form of the socket 110 and the arm 230.

The openings 220 extend transversally to the arms 230, that is, tangentially to an arc of a circle centred on the socket 110. They can be blind holes and terminate transversally only on a lateral face of the arm 230, or be through holes.

The anchoring element 210 is preferably a cam mounted mobile in rotation about an axis of rotation extending through the opening 220, in a direction substantially parallel to the direction of insertion of the socket in its cavity L, between a retracted position, in which the cam 210 is confined in the opening 220, and an anchoring position, in which at least one part of the cam 210 projects out from the opening 220 and meets with a lateral wall of the cavity L, that is, with an osseous wall.

In addition, in this first embodiment, the system 200 further comprises an actuation element 213 which cooperates with the cam 210, adapted for setting the cam 210 in rotary motion between its retracted position and its anchoring position.

For this, above the opening and at the level of the axis of rotation of the cam, the arm 230 has a through orifice 232 adapted to receive the actuation element 213.

Figure 2A:
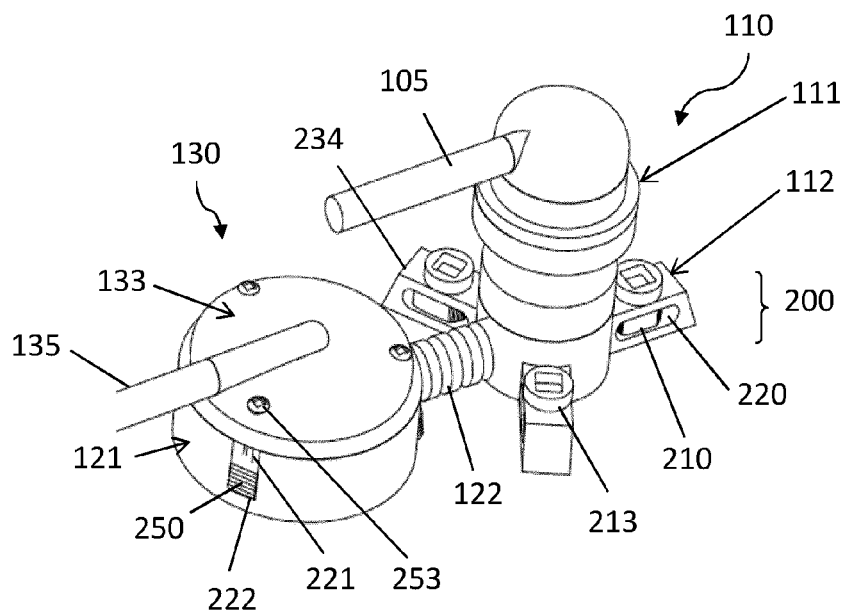
FIG. 2A illustrates a cranial connection assembly according to a third embodiment.

The actuation element can comprise a rod whereof one end cooperates with the cam 210, and an actuation head. For example, as illustrated in FIG. 2A, the end of the rod has a hexagonal cross-section and is adapted to be inserted in a hexagonal hole 214 made through the cam 210, at the level of its axis of rotation (see FIG. 4). In addition, the form of the head of the actuation element 213 is adapted to cooperate with a tool, such as a screwdriver. For this, the head can have a groove, a blind, square, polygonal, or any other form of bore designed to cooperate with the tool.

The rod is therefore inserted in through the orifice 232 into the hole 214 corresponding to the cam 210, whereas the actuation head rests on an upper surface of the arm 230, accessible to an operator. Rotation of the actuation head by a tool then causes rotation of the rod and therefore of the cam 210 inside the opening 220.

Figure 4:
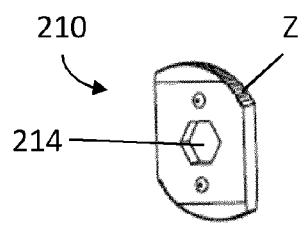
FIG. 4 illustrates an anchoring cam used for anchoring a cranial connection assembly according to the second, third, or fourth embodiments.
Figure 5:
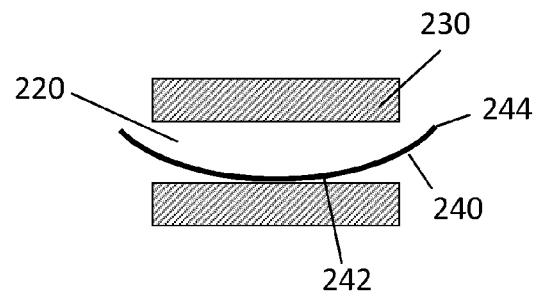
FIG. 5 illustrates anchoring means according to another embodiment.

As shown in FIG. 4, the external surface of the cam 210, designed to cooperate with the osseous wall, preferably has a curved form diverging in the direction of anchoring to improve the solidity of the anchoring of the socket in the cavity L.

In the embodiment of FIG. 2A, the opening 220 is a through hole and the cam 210 has central symmetry, such that when in the anchoring position it is meshed at the level of two anchoring zones opposite the internal wall of the cavity L.

By way of variant, the opening is blind and/or the centre of rotation of the cam 210 is eccentric relative to its centre of symmetry, such that the cam 210 progressively meshes with the internal wall of the cavity L when it passes from the retracted position to the anchoring position.

Moreover, each arm 230 of the anchoring system 200 can have a cross-section, in the radial direction, to facilitate insertion of the anchoring element in the cavity and if required an inclined cross-section 234 at the level of its free end to prevent withdrawal of the socket 110 after osseous growth.

Figure 2B:
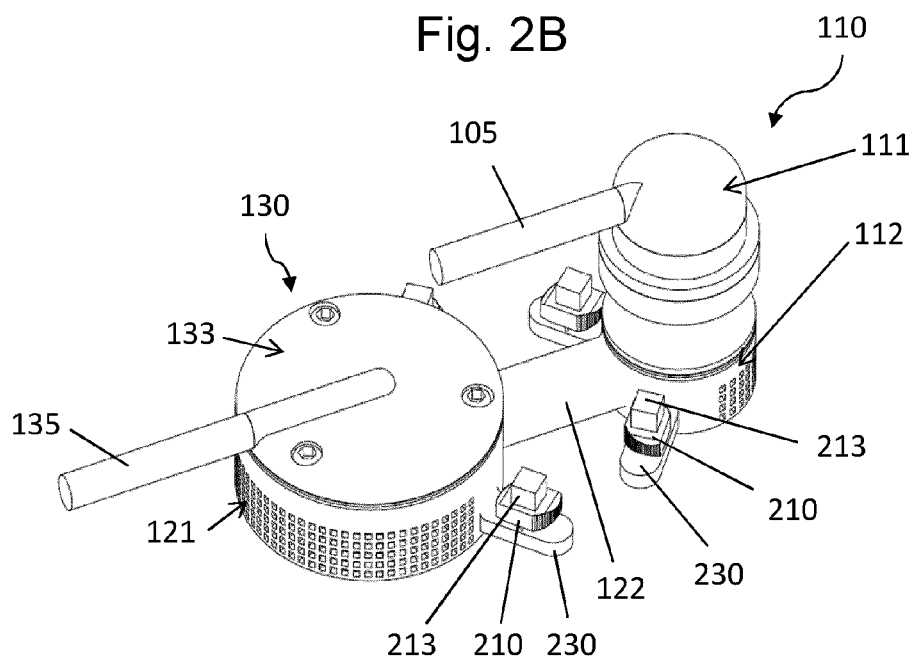
FIG. 2B illustrates a cranial connection assembly according to a fourth embodiment.
Figure 2C:
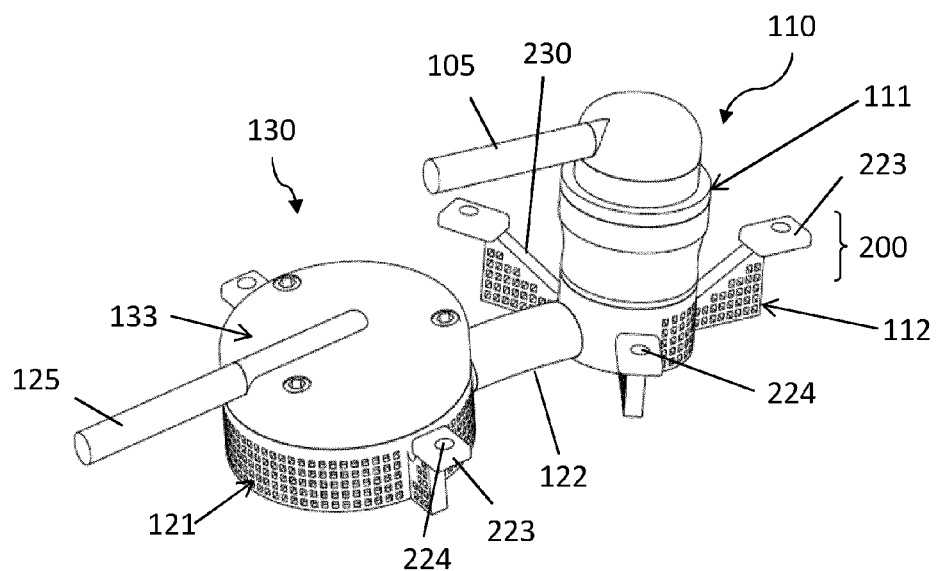
FIG. 2C illustrates a cranial connection assembly according to a fifth embodiment.

In addition, as is shown in FIG. 2B, it is not necessary for the anchoring arm 230 to comprise an opening 220 to confine the cam 210. In fact, according to a simpler embodiment, the arm 230 is a longitudinal bar on which the cam 210 is mounted in rotation. The coupling between the cam 210 and the arm 230 can likewise be done by means of a rod forming the axis of rotation of the cam 210, and having an actuation head 213 for meshing said cam 210 with the lateral wall of the osseous cavity L. In the retracted position, the cam 210 is superposed along the arm 230, with their longitudinal axes being substantially parallel.

Figure 2D:
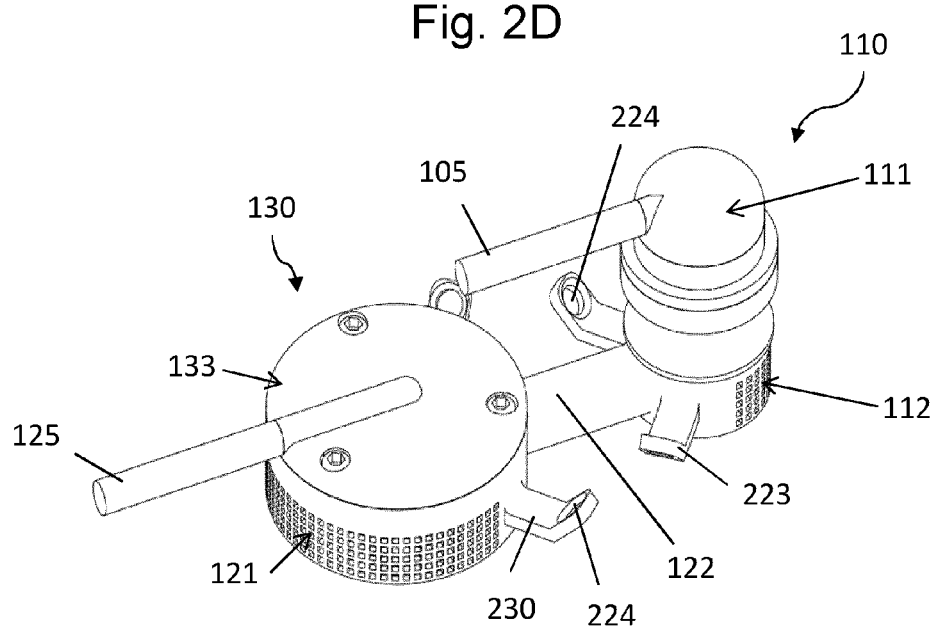
FIG. 2D illustrates a cranial connection assembly according to a sixth embodiment.
Figure 2E:
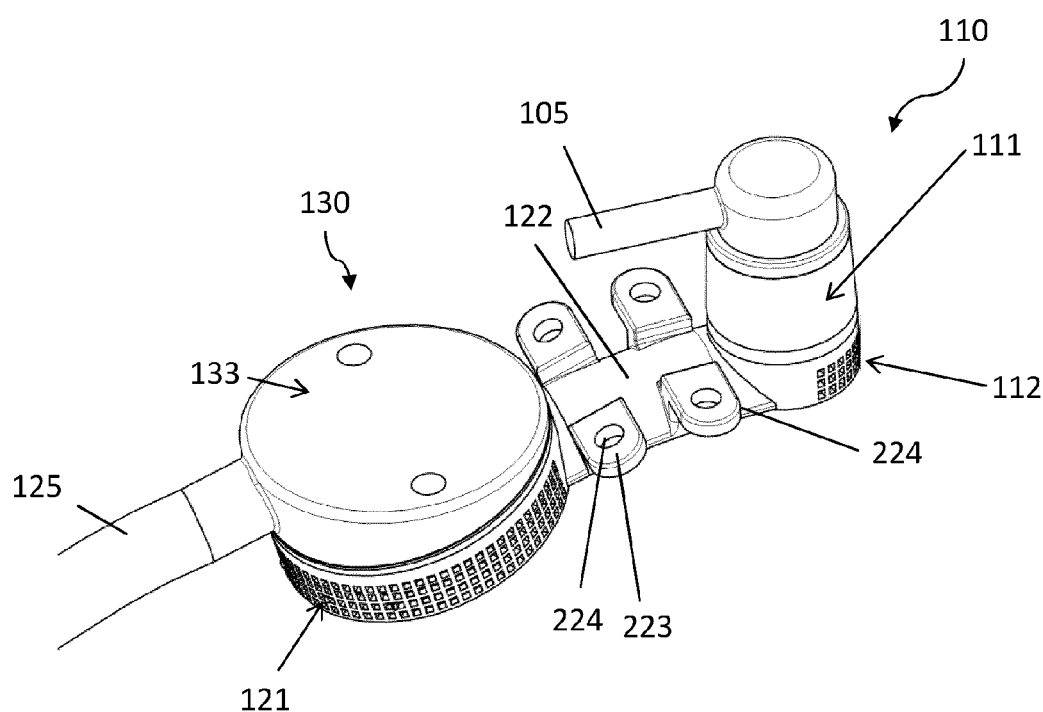
FIG. 2E illustrates a cranial connection assembly according to a seventh embodiment.

According to another embodiment, illustrated in FIG. 2D, the anchoring means 240 are elastic strips inserted into the openings 220 made in the anchoring arm 230 tangentially to the arc of a circle centred on the socket and adapted to lean against the internal wall of the cavity L when the socket 110 is inserted forcefully into the cavity L. In this case, positioning of the socket 110 in the cavity L corresponds to impaction since this socket 110 is positioned forcefully in the cavity L, the elastic strips being in contact with the osseous wall as soon as the socket 110 is inserted.

Preferably, in this embodiment the openings are through holes such that the two ends of each elastic strip 240 protrude out from the arms 230. In this way, when the socket 110 is inserted forcefully into the cavity L, each elastic strip is stressed in flexion by the internal walls of the cavity L and bends, the concavity 242 of the strips being directed to the bottom of the cavity L, whereas the ends 244 of the strips 240 are directed to the opening of the cavity L.

Once the socket 110 is inserted in the cavity L, and by plating the base 112 of the socket 110 to the bottom of the cavity L, the ends 244 of the elastic strips are pressed against the internal walls: the central part 242 of the elastic strips exerts force on the opening 220 towards the bottom of the cavity L.

It is understood advantageously that in this embodiment any traction on the socket 110 tending to withdraw it from the cavity L increases the anchoring of the strips 240 in the internal walls of the cavity L.

In the case of blind openings 220, one of the ends of the strips 240 can be fixed on a wall of the opening 220 to prevent it from exiting from the opening 220 during insertion of the socket 110 in the cavity L.

According to yet another embodiment, illustrated in FIG. 2A in relation to the cranial electric connection element 130, the openings 221 can be made directly in the base of the device to be hooked. They are blinds and terminate laterally, as illustrated in FIG. 1C.

Each opening 221 contains a rack 250, guided in translation against an inclined wall 222 arranged at the bottom of the opening 221 between a retracted position in which it is confined in the opening 221, and an anchoring position in which it projects out from the opening 221 and meshes with the internal wall of the cavity L.

Again, the rack 250 is meshed with the wall by an actuation element 253 which can be for example a screw which pushes the rack 250 towards its anchoring position.

Irrespective of the embodiment of the anchoring element (cam 210, rack 250, strip 240, etc.), the latter comprises an anchoring zone Z on the internal walls of the cavity which may have surface irregularities to increase friction with the wall and therefore the solidity of the anchoring. Moreover, after osseous cicatrisation such irregularities augment the contact surface between the bone and the implant. Typically, in the case of cams, this anchoring zone Z corresponds to the part of the external surface of the cams 210 which is in contact with the wall in the anchoring position, whereas in the case of the strips 240 this is the end 244 of the strips at the level of which said strip 240 is pressed.

Examples of surface irregularities are projecting portions extending perpendicularly to the direction of the anchoring restriction between the anchoring element and the wall. Such projecting portions may have the shape of teeth, rough spots, or any other adapted profile as illustrated through FIGS. 7A, 7B, 7C, and 7D.

Such projecting portions located forward and backward of the intra-osseous walls of the device are designed to obtain an initial stabilization by impaction of the device, stabilization requiring an insertion force inferior to the breakout force, as a result of the geometry of the projections on the socket 110 and extension member 120.

The projecting portions have a geometric shape to provide a retention effect, said shape being preferably chosen among a cone shape, a pyramid shape, and/or a polyhedron shape. Alternatively the projecting portions may have an asymmetric geometric shape to provide a retention effect.

Preferably, the projecting portions have a length comprised between 20 micrometers and 2000 micrometers, and preferably of around 400 micrometers, which correspond to the depth up to which they penetrate the lateral wall of the cavity (L).

An important advantage derived from the configuration proposed for the intra-osseous anchoring system 200 is that it can be actuated automatically by a robot for example, such that placing the corresponding intra-osseous implant can be done in minimal time, all the more reducing surgical intervention time.

The cranial connection assembly 110, 120 can likewise be anchored by other means, especially using osteosynthesis screws as is shown in FIGS. 2C, 2D, 2E, 8A, 8B and 8C in case of a realisation of a cavity L, which size is superior than the dimensions of the elements 110, 120. The screws 261 can be fixed on an anchoring support 260 removable from the elements 110, 120 as shown in FIGS. 8D, 8E and 8F.

Figure 8A:
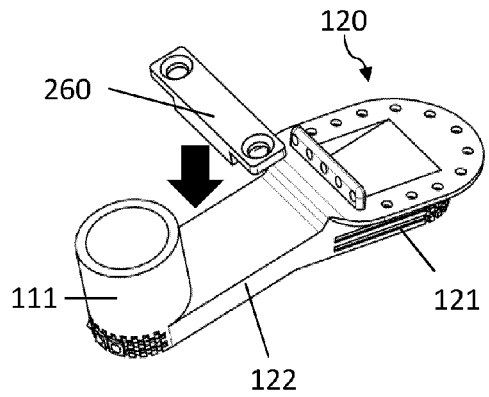
FIG. 8A illustrates an independent anchoring mean support before its adjunction to the percutaneous socket.
Figure 8B:
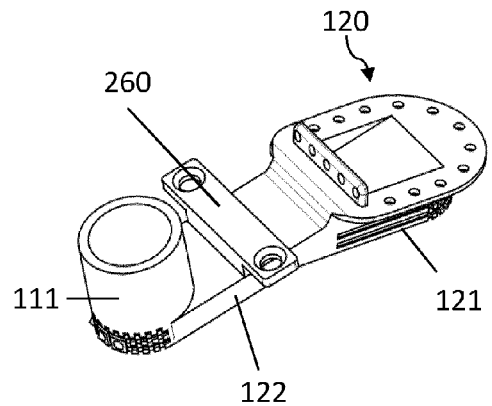
FIG. 8B illustrates the independent anchoring mean support of FIG. 8A being positioned on the percutaneous socket.
Figure 8C:
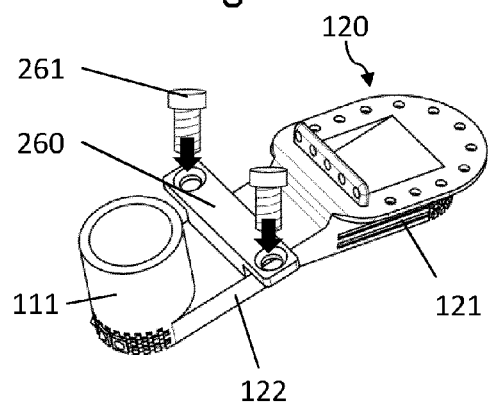
FIG. 8C illustrates osteosynthesis screws being inserted in the anchoring mean support of FIGS. 8A and 8B.
Figure 8D:
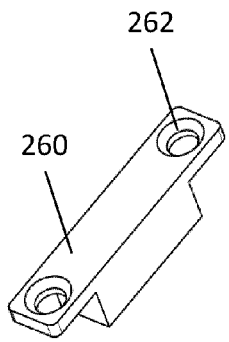
FIG. 8D illustrates the independent anchoring mean support of FIG. 8A.
Figure 8E:
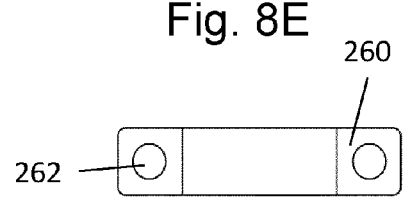
FIG. 8E illustrates a top view of the independent anchoring mean support of FIG. 8D.
Figure 8F:
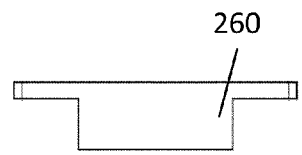
FIG. 8F illustrates a side view of the independent anchoring mean support of FIG. 8D.

In this way, the anchoring means are arranged to form anchoring points along the longitudinal axis of the extension member 120, for example on either side of the extension member 120, as is illustrated in FIGS. 2B and 2D, and 8C.

As mentioned earlier, all or part of the pieces described can be made by additive technology, for example according to the technique of selective laser fusion. This method is an additive production of metals technology which is based on the use of a high-power laser for fusing fine metallic powders to form, layer by layer, metallic portions defined according to a computer-aided design model (CAD). Once a metallic layer has been created, the apparatus operating according to this technology of laser fusion deposits a fresh layer of powder designed to fuse to form the next metallic layer and form the piece by successive superposition of layers of variable thickness according to the apparatus used, where this thickness can be for example of the order of 20 to 100 micrometers. The apparatus can be used with various types of metallic powders to form high-density pieces from material such as stainless steel or tool steel, titanium, chrome-cobalt, aluminium, and many other alloys. In this case, the selective laser fusion technique is particularly advantageous for forming dense pieces from titanium or titanium-based alloys.

The pieces can therefore be made to measure, irrespective of their form, which optimise production costs and time, while having pieces made precisely.

The different elements forming the cranial connection assembly 110, 130 can be made independently from each other, or even possibly in a single piece if this assembly is monobloc as described earlier.

It should be noted that the cranial connection assembly 110, and the extension member 120 could likewise be made conventionally, especially by milling and electro-subtraction.

Moreover, that device as well as the cranial and thoracic connector are not necessarily metallic and could be made of another material such as zirconium.

The invention claimed is:

1. A permanent percutaneous electric connection device intended to be fixed in an osseous structure of a patient to electrically connect an internal entity located inside the body of the patient to an entity external to said body, wherein:
   the device encloses electric connection means running from a first connector to be connected to the external entity to a second connector to be connected to the internal entity, and
   the device comprises:
      a percutaneous socket having a first end comprising the first connector to be connected to the external entity and a second end opposite to the first end,
      an extension member extending from the second end of the socket forming an angle relative to the socket and being designed to shift the second connector away from the socket by a non-zero distance, wherein the extension member is further designed for full osseous burial into the osseous structure with a free end of the extension member being substantially flush with the surface of said osseous structure, and
      an electric connection member securely fastened to the free end of the extension member, said electric connection member comprising the second connector,
   wherein the base of the socket has a surface with projecting portions protruding therefrom, said projecting portions forming means for anchoring the socket in a cavity made in the osseous structure and being designed to penetrate the lateral wall of the cavity in a depth between 20 micrometers and 2000 micrometers.

2. The device as claimed in claim 1, wherein the percutaneous socket comprises a percutaneous abutment arranged on an anchoring base, wherein:
   the percutaneous abutment comprises the first connector to the external entity,
   the extension member extends from the anchoring base, said anchoring base being designed for full osseous burial in the osseous structure so that the percutaneous abutment protrudes relative to the surface of the osseous structure.

3. The device as claimed in claim 2, wherein the anchoring base and the percutaneous abutment are monobloc.

4. The device as claimed in claim 2, wherein the anchoring base and the percutaneous abutment are removable from each other.

5. The device as claimed in claim 1, wherein the anchoring base of the socket and the extension member are monobloc.

6. The device as claimed in claim 1, wherein the extension member and the electric connection member are monobloc.

7. The device as claimed in claim 1, wherein the second end of the socket and the free end of the extension member are separated by a non-zero distance of at least 5 mm.

8. The device as claimed in claim 1, wherein the extension member comprises a longitudinal portion extending from the socket and a cup-shaped portion forming the free end of said extension member.

9. The device as claimed in claim 8, wherein the cup-shaped portion is based on a geometry chosen among circular, regular polygonal, irregular polygonal, or a combination thereof.

10. The device as claimed in claim 1, wherein the electric connection member comprises an extra-osseous lid to be securely fastened onto the free end of the extension member, wherein the second connector is arranged within said extra-osseous lid.

11. The device as claimed in claim 1, wherein the electric connection member comprises:
    an extra-osseous electric connection element comprising the second connector, and
    a flexible intermediate element for bringing the connection means from the extension member to the extra-osseous electric connection element, wherein the flexible intermediate element is securely fastened to the free end of the extension member on the one hand and to the extra-osseous electric connection element on the other hand.

12. The device as claimed in claim 11, wherein the flexible intermediate element is overmold onto the free end of the extension member and/or onto the extra-osseous electric connection element.

13. The device as claimed in claim 11, wherein the flexible intermediate element comprises a mechanical relief system for preventing elongation of the connection means along their longitudinal axis.

14. The device as claimed in claim 13, wherein the mechanical relief system comprises a textile structure or a biocompatible metallic structure such as a titanium structure.

15. The device as claimed in claim 1, wherein the socket and the electric connection member have mean planes forming together an angle $\alpha$ of between 0.5° and 40°.

16. The device as claimed in claim 1, wherein the socket and the electric connection member have mean planes parallel to each other.

17. The device as claimed in claim 1, wherein the socket and/or the extension member have walls in which are made cavities to form honeycomb walls in order to enlarge the surface of contact between the device and an osseous structure into which the device is to be fixed.

18. The device as claimed in claim 1, wherein the socket and/or of the extension member comprise an intra-osseous anchoring system including:
    an anchoring base designed to be inserted in the cavity according to a direction of insertion perpendicular to the bottom of said cavity, and
    at least one anchoring element arranged so as to be able to protrude relative to the anchoring base parallel to the bottom of the cavity to mesh with a lateral wall of said cavity.

19. The device as claimed in claim 1, wherein said projecting portions are designed to penetrate the lateral wall of the cavity in a depth of 400 micrometers.

20. The device as claimed in claim 1, wherein the projecting portions have a geometric shape to provide a retention effect, said shape being a symmetric shape chosen among a cone shape, a pyramid shape, and/or a polyhedron shape.

21. The device as claimed in claim 1, further comprising a removable anchoring member to be positioned onto the extension member, wherein said removable anchoring member comprises a main body and at least two plates extending from the main body in order to form a shouldering so as to be flush with the surface of the osseous structure at the periphery of the cavity, each plate having at least one through orifice intended to receive an osteosynthesis screw for anchoring in the osseous structure.

22. The device as claimed in claim 1, wherein the connectors comprise contactless connection means, adapted for transfer of energy or any electrical signal.

23. The device as claimed in claim 1, wherein the second connector is designed for detachable connection of a cable intended to be connected to the internal entity.

24. The device as claimed in claim 1, further comprising an intermediate connection assembly, intended to be arranged between the electric connection member and the internal entity and adapted to be fixed in the body of the patient.

25. The device as claimed in claim 24, wherein the intermediate connection assembly further comprises an auxiliary socket adapted to be connected to an external power supply, the intermediate connector and the auxiliary socket being electrically connected by an intermediate connecting element.

26. The device as claimed in claim 1, wherein the second connector is designed for detachable connection of a cable intended to be connected to the internal entity, the device further comprising:
    an intermediate connection assembly, intended to be arranged between the electric connection member and the internal entity and adapted to be fixed in the body of the patient; and
    an electric cable connected detachably to the electric connection member on the one hand and to the intermediate connection assembly on the other hand.

27. The device as claimed in claim 1, wherein the second end of the socket and the free end of the extension member are separated by a non-zero distance of at least 5 mm, and less than 20 mm.

28. The device as claimed in claim 1, wherein the second end of the socket and the free end of the extension member are separated by a non-zero distance equal to 10 mm.

29. The device as claimed in claim 1, wherein the extension member comprises an elongated portion and an extremity forming the free end of the extension member.

30. The device as claimed in claim 1, wherein the socket and the electric connection member have mean planes forming together an angle $\alpha$ of between 1° and 30°.

31. The device as claimed in claim 1, wherein the socket and the electric connection member have mean planes forming together an angle $\alpha$ of 15°.

32. A permanent percutaneous electric connection device intended to be fixed in an osseous structure of a patient to electrically connect an internal entity located inside the body of the patient to an entity external to said body, wherein:
    the device encloses electric connection means running from a first connector to be connected to the external entity to a second connector to be connected to the internal entity, and
    the device comprises:
        a percutaneous socket having a first end comprising the first connector to be connected to the external entity and a second end opposite to the first end,
        an extension member extending from the second end of the socket forming an angle relative to the socket and being designed to shift the second connector away from the socket by a non-zero distance, wherein the extension member is further designed for full osseous burial into the osseous structure with a free end being substantially flush with the surface of said osseous structure, and
        an electric connection member securely fastened to the free end of the extension member, said electric connection member comprising the second connector,
    wherein the base of the socket and the extension member have both a surface with projecting portions protruding therefrom, said projecting portions forming means for anchoring the socket and the extension member respectively in a cavity made in the osseous structure.

* * * * *